United States Patent
Heinecke et al.

[11] Patent Number: 5,374,505
[45] Date of Patent: Dec. 20, 1994

[54] COLOR PHOTOGRAPHIC RECORDING MATERIAL FOR THE PRODUCTION OF COLOR IMAGES

[75] Inventors: Jürgen Heinecke, Leichlingen; Helmut Mäder, Odenthal; Fritz Nittel, Leverkusen; Hans Öhlschläger, Bergisch Gladbach; Armin Voigt, Cologne, all of Germany

[73] Assignee: Agfa-Gevaert AG, Leverkusen, Germany

[21] Appl. No.: 107,350

[22] Filed: Aug. 16, 1993

[30] Foreign Application Priority Data

Aug. 28, 1992 [DE] Germany .............. 4228652
Apr. 1, 1993 [DE] Germany .............. 4310703

[51] Int. Cl.$^5$ .............................. G03C 1/46
[52] U.S. Cl. .............................. 430/504; 430/631; 430/607; 430/611; 430/613; 430/546; 430/551
[58] Field of Search ............... 430/504, 631, 546, 607, 430/611, 613, 551

[56] References Cited

U.S. PATENT DOCUMENTS

| | | |
|---|---|---|
| 4,474,873 | 10/1984 | Maekawa et al. ........... 430/631 |
| 4,610,954 | 9/1986 | Torigoe et al. .............. 430/611 |
| 4,816,290 | 3/1989 | Heki et al. ................... 430/631 |
| 4,840,871 | 6/1989 | Peters et al. ................. 430/611 |
| 4,959,298 | 9/1990 | Mitsui et al. ................. 430/611 |

*Primary Examiner*—Charles L. Bowers, Jr.
*Assistant Examiner*—Geraldine Letscher
*Attorney, Agent, or Firm*—Connolly & Hutz

[57] ABSTRACT

A color photographic recording material containing, on a layer support, at least one blue sensitive silver halide emulsion layer and a yellow coupler associated therewith, at least one green sensitive silver halide emulsion layer and a magenta coupler associated therewith and at least one red sensitive silver halide emulsion layer and a cyan coupler associated therewith also contains, in a layer which is not sensitive to light, a compound corresponding to formula I (stabilizer)

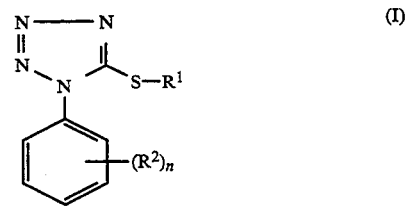

wherein
$R^1$ denotes H or a group which can be split off under alkaline development conditions;
$R^2$ denotes H, halogen, OH, an alkyl having 1 to 4 carbon atoms, an alkoxy having 1 to 4 carbon atoms, $COOR^3$, $CONR^4R^5$, $SO_2NR^4R^5$, $NH-COR^3$, $NH-SO_2-R^3$ or $NH-CO-NHR^4$;
$R^3$ denotes an alkyl having 1 to 4 carbon atoms,
$R^4$ and $R^5$ denote H or a group such as $R^3$ and
n denotes 1, 2 or 3 in combination with 1- to 5-times its quantity by weight of a dispersing agent. The incorporated stabilizer suppresses the formation of magenta color fogs in the bleach fixing bath.

18 Claims, No Drawings

COLOR PHOTOGRAPHIC RECORDING MATERIAL FOR THE PRODUCTION OF COLOR IMAGES

This invention relates to a light-sensitive colour photographic recording material suitable for rapid processing, comprising a layer support and, arranged on the layer support, at least three light-sensitive silver halide emulsion layers differing in spectral sensitivity which are spectrally associated with, respectively, a cyan coupler, a magenta coupler and a yellow coupler. At least one of the layers of the colour photographic recording material according to the invention contains a stabilizer compound in combination with a special dispersing agent.

It is known to produce coloured photographic images my chromagenic development, i.e. by developing imagewise exposed silver halide emulsion layers by means of suitable colour producing developer substances, so-called colour developers, in the presence of suitable colour couplers, the oxidation product of the developer substances produced in correspondence with the silver image reacting with the colour coupler to form a dye image. The colour developers used are normally aromatic compounds containing primary amino groups, in particular compounds of the p-phenylene diamine series.

One important precondition for the rapid processing of colour photographic recording materials is the use of emulsions which can be developed rapidly. Silver halide emulsions which are rich in chloride have proved to be advantageous in this respect. Emulsions of this type are described, for example, in U.S. Pat. No. 4,269,927 and WO 87/04534. Emulsions having a chloride content of at least 80 mol-%, preferably from 95 to 100 mol-%, are particularly suitable.

The colour couplers and the dyes obtained from them by chromogenic development are required to meet various demands in particular with regard to rapid development. Thus the speed of coupling of the colour couplers with the oxidation product of the colour developer should be as great as possible and the highest possible maximum colour density should be obtainable; further, the colour couplers and the dyes obtained from them must be sufficiently stable to light, elevated temperature and moisture. This applies both to fresh material and to processed material.

For example, the residual coupler still present in the image whites of the processed material must not undergo yellowing and the dyes must be sufficiently resistant to gaseous reducing of oxidizing agents. They must also be fixed in a diffusion-fast form in the image layer and should be deposited as a very fine grain during chromogenic development. Finally, the dyes obtained from the colour couplers by chromogenic development must have a suitable absorption curve with a maximum corresponding to the colour of the desired partial image and their side absorptions should be low.

The colour images obtained from rapid processing frequently have undesirable coloured fogs, in particular magenta coloured fogs, which are superimposed on the colour image proper. It is presumed that this is due to an unwanted after-development which takes place in the bleach fixing bath in the presence of complex dissolved silver ions when colour developers are carried into the bath so that additional dye is formed. These fogs are particularly disturbing in those parts of the image in which relatively little dye has been developed in the colour developer, in particular magenta dye.

It is an object of this invention to provide a colour photographic recording material which is suitable for rapid processing and in which the occurrence of the colour fogs can be avoided. It has been found that this may be achieved if at least one of the layers of the colour photographic recording material contains a stabilizer compound in combination with a special dispersing agent.

The invention relates to a colour photographic recording material containing, on a layer support, at least one blue sensitive silver halide emulsion layer and a yellow coupler associated therewith, at least one green sensitive silver halide emulsion layer and a magenta coupler associated therewith and at least one red sensitive silver halide emulsion layer and a cyan coupler associated therewith as well as other, light insensitive layers, characterised in that the recording material contains, in at least one light insensitive layer, a compound corresponding to formula I (stabilizer)

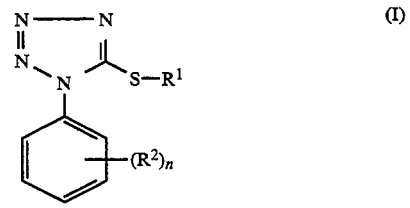

wherein
  $R^1$ denotes H or a group which can be split off under alkaline development conditions;
  $R^2$ denotes H, halogen, OH, an alkyl group having 1 to 4 carbon atoms, an alkoxy group having 1 to 4 carbon atoms $COOR^3$, $CONR^4R^5$, $SO_2NR^4R^5$, $NH-COR^3$, $NH-SO_2-R^3$ or $NH-CO-NHR^4$;
  $R^3$ denotes an alkyl group having 1 to 4 carbon atoms,
  $R^4$ and $R^5$ denote H or a group such as $R^3$ and
  n denotes 1, 2 or 3
in combination with 1- to 5-times the quantity by weight of a dispersing agent.

A group denoted by $R^1$ in formula I capable of being split off under alkaline development conditions may be, for example, an acyl group derived from a carbonic acid monoester, e.g. an alkoxycarbonyl, a cycloalkylcarbonyl or an aroxycarbonyl group.

A halogen atom denoted by $R^2$ in formula I may be, for example, a chlorine or bromine atom.

The alkyl groups denoted by $R^2$ and $R^3$ in formula I may be straight chain or branched and substituted or unsubstituted; examples are methyl, ethyl, propyl, isopropyl, butyl, methoxymethyl, methylthioethyl, chloroethyl, carboxymethyl-thiomethyl and carboxyethyl.

Examples of compounds corresponding to formula I (stabilizers) are given in Table 1 below.

TABLE 1

| I- | $R^1$ | $R^2$ |
|---|---|---|
| 1 | H | H |
| 2 | $-COOC_2H_5$ | H |
| 3 | $-COO-\phi$ | H |
| 4 | H | $3-NH-COCH_3$ |
| 5 | H | $4-CH_3$ |

TABLE 1-continued

| I- | R¹ | R² |
|---|---|---|
| 6 | —COOCH(CH₃)₂ | H |
| 7 | H | 4-OH |
| 8 | H | 3-SO₂NH₂ |
| 9 | —COOCH₂CH(CH₃)₂ | H |
| 10 | —COOC₄H₉ | H |
| 11 | H | 3-Cl, 4-CH₃ |
| 12 | H | 3,4-di-Cl |
| 13 | —COOC₄H₉ | 3,4-di-Cl |
| 14 | 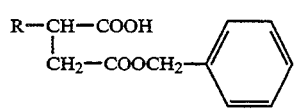 | 3,4-di-Cl |
| 15 | 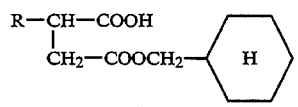 | H |
| 16 | H | 3-OH |
| 17 | H | 3-NH—CO—NH—CH₃ |
| 18 | 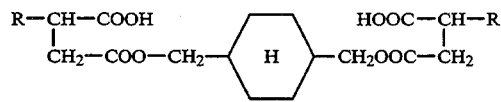 | H |
| 19 | 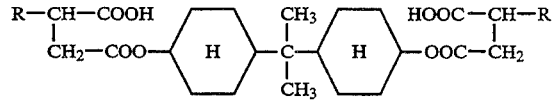 | 3,4-di-Cl |
| 20 | —COOC₂H₅ | 3,4-di-Cl |
| 21 | H | 4-SO₂NH₂ |
| 22 | H | 4-Cl |
| 23 | H | 3,4-di-CH₃ |
| 24 | H | 4-NH—CO—CH₂—O—CH₃ |
| 25 | —COOC₄H₉ | 3-NH—COCH₃ |

TABLE 1-continued

| I- | R¹ | R² |
|---|---|---|
| 26 | H | 4-COOC₂H₅ |
| 27 | H | 4-NH—CO—(CH₂)₂—S—CH₃ |
| 28 | H | 3-NH—COCH₂S—CH₂COOH |
| 29 | H | 3-NH—CO(CH₂)₂COOH |
| 30 | 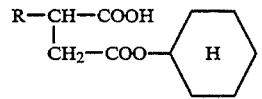 | 3,4-di-Cl |
| 31 | —COOC₂H₅ | 3-NH—CO—CH₂—S—CH₃ |

The dispersing agent used according to the invention is a compound having at least one hydrophilic group and a hydrophobic group containing at least one alkyl or cycloalkyl group with not less than 6 carbon atoms, preferably not less than 10 carbon atoms. The following are examples of hydrophilic groups: Carboxyl, sulpho, hydroxyl and quaternary ammonium groups. Examples of suitable dispersing agents according to the present invention include aliphatic, cycloaliphatic and aromatic carboxylic acids having at least one optionally unsaturated aliphatic or cycloaliphatic group with not less than 6 carbon atoms, preferably not less than 10 carbon atoms. Such compounds are described, for example, in DE-A-1 772 192, DE-A-20 42 659, DE-A-20 49 689, DE-A-30 24 881 and DE-A-36 13 974. Monoesters of fatty succinic acids have proved to be particularly advantageous; examples of these are given below (Compounds II-1 to II-21):

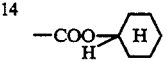

II-1

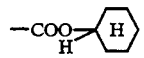

II-2

II-3

II-4

II-5

II-6

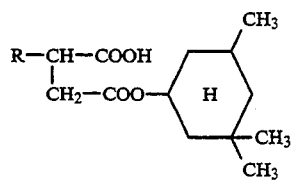
II-7
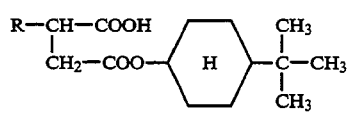
II-8
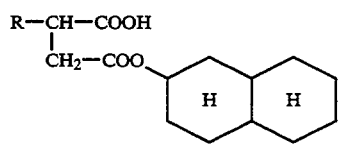
II-9
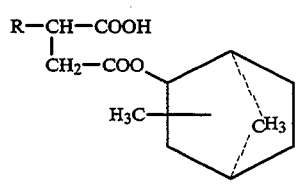
II-10
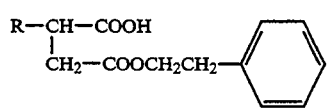
II-11
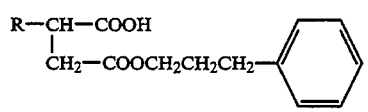
II-12
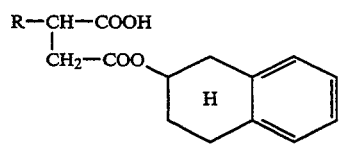
II-13
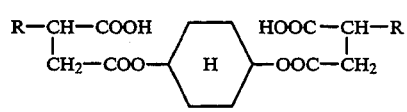
II-14
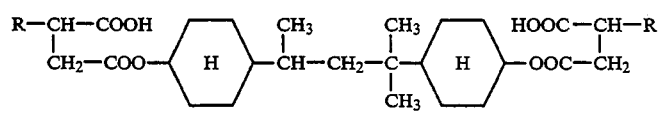
II-15
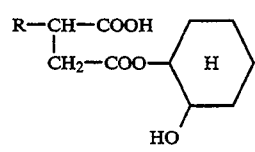
II-16
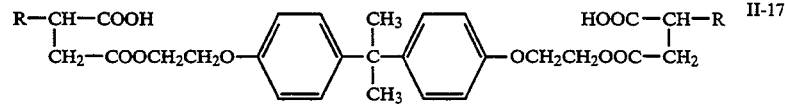
II-17
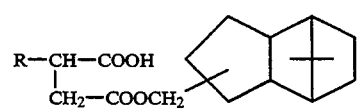
II-18

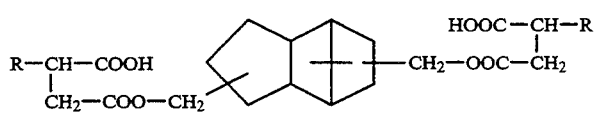 II-19

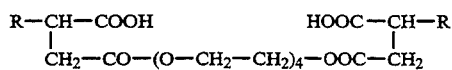 II-20

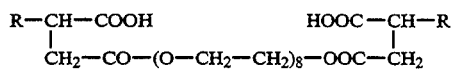 II-21

In formulae II-1 to II-21, the symbol R stands for a relatively long chain aliphatic group having at least 6 carbon atoms. This group is preferably one of the following monounsaturated aliphatic groups: $C_{12}H_{23}$, $C_{15}H_{29}$ or $C_{18}H_{35}$, the formation of which can be explained by multiple addition of propylene.

The compounds II-1 to II-21 are not necessarily single substances but may be mixtures of several substances of the type mentioned.

Compounds containing a quaternary ammonium group as shown in the following formula are also suitable dispersing agents according to the present invention:

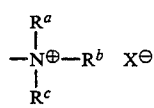

wherein $R^a$, $R^b$ and $R^c$ stand for alkyl with 1–4 carbon atoms and $X^\ominus$ stands for an external anion, e.g. $Cl^\ominus$, $NO_3^\ominus$ or $\frac{1}{2}(SO_4^{2\ominus})$, and among these compounds, those having a quaternary ammonium group corresponding to the following formula are particularly preferred:

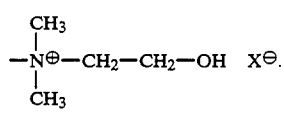

The following (compounds II-22 to II-31) are examples of suitable dispersing agents containing a quaternary ammonium group:

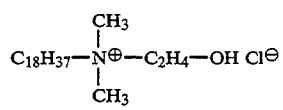 II-22

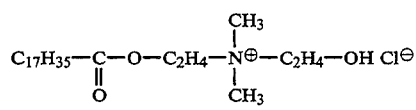 II-23

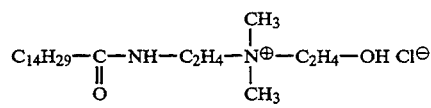 II-24

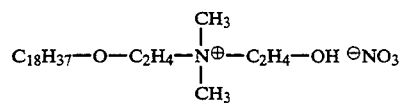 II-25

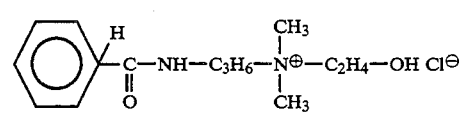 II-26

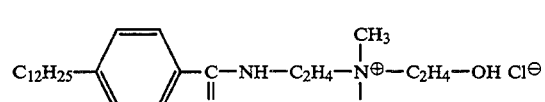 II-27

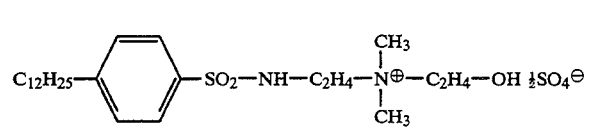 II-28

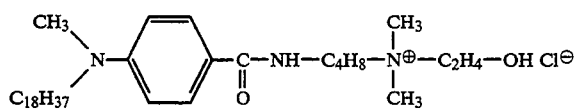 II-29

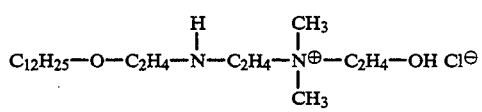 II-30

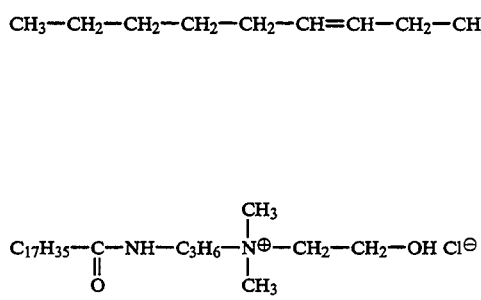 II-31

$$C_{17}H_{35}-\underset{\underset{O}{\|}}{C}-NH-C_3H_6-\underset{\underset{CH_3}{|}}{\overset{\overset{CH_3}{|}}{N^\oplus}}-CH_2-CH_2-OH \quad Cl^\ominus$$ II-32

Dodecylbenzene sulphonic acid and sulphosuccinic acid dioctyl ester are examples of dispersing agents according to the invention containing a sulpho group.

According to the present invention, a stabilizer and a dispersing agent are together added to a light-insensitive layer of a colour photographic recording material. These substances are suitably incorporated by first forming a dispersion from the stabilizer and dispersing agent in an aqueous medium optionally containing a binder and then using this dispersion as casting solution for the given light-insensitive layer or adding it to a casting solution for such a layer. A stabilizer dispersion suitable for incorporation may be prepared, for example, as follows:

An aqueous (gel) phase is produced by dissolving 667 g of gelatine and 19 g of phenol in 5985 ml of water (6671 g—Component 1).

An "oily" phase is produced by dissolving 100 g of stabilizer (Compound I-7) and 240 g of dispersing agent (Compound II-32) in 147 ml of ethanol and making up to 347 g with water (Component 2). Component 2 is stirred into Component 1. The mixture is homogenised and concentrated to 700 ml by evaporation in a vacuum and may then be added to the casting solution for the given light insensitive layer so that this layer contains the stabilizer in a quantity of from 0.1 to 5.0 mg/m$^2$, preferably from 0.2 to 2.5 mg per m$^2$.

The combination of stabilizer and dispersing agent is preferably added to a light insensitive layer adjacent to the layer containing the magenta coupler, most preferably to the light insensitive layer situated just above the magenta layer. The combination of stabilizer and dispersing agent may also be used in a light sensitive silver halide emulsion layer which contains coupler, where it may counteract the occurrence of coloured streaks but when used in this way it is difficult to avoid a loss of sensitivity.

A suitable support for preparing the colour photographic material, is, for example, paper laminated with a baryta layer of with an α-olefin polymer layer (e.g. polyethylene). Such supports may be coloured with dyes and pigments, for example titanium dioxide. The surface of the support is generally subjected to a treatment for improving the adherence of the photographic emulsion layer, for example a corona discharge followed by application of a subbing layer. Transparent supports may be used for the production of transparent colour images, for example for display materials, e.g. films and sheets of synthetic or semi-synthetic polymers such as cellulose nitrate, cellulose acetate, cellulose butyrate, polyethylene terephthalate or the like.

Binders, silver halide grains and colour couplers are essential components of the photographic emulsion layers.

The binder used is preferably gelatine but this may be partly or completely replaced by other synthetic, semi-synthetic or naturally occurring polymers. Examples of synthetic gelatine substitutes include polyvinyl alcohol, poly-N-vinyl pyrrolidone, polyacrylamides, polyacrylic acid and derivatives thereof, in particular their copolymers. Examples of naturally occurring gelatine substitutes include other proteins such as albumin or casein, cellulose, sugar, starch and alginates. Semi-synthetic gelatine substitutes are generally modified naturally occurring products. Cellulose derivatives such as hydroxyalkyl cellulose, carboxymethyl cellulose and phthaloyl cellulose and gelatine derivatives obtained by reaction with alkylating or acylating agents or by the grafting of polymerisable monomers are examples of these.

The binders should have a sufficient number of functional groups available so that sufficiently resistant layers may be produced by reaction with suitable harden ers. Such functional groups are in particular amino groups but also carboxyl groups, hydroxyl groups and active methylene groups.

Gelatine, which is preferably used, may be obtained by acid or alkaline decomposition or an oxidized gelatine may be used. The preparation of such gelatines is described, for example, in "The Science and Technology of Gelatine", published by A. G. Ward and A. Courts, Academic Press 1977, page 295 et seq. Whichever gelatine is used, it should be as free as possible from photographically active impurities (inert gelatine). Gelatines having a high viscosity and low tendency to swell are particularly advantageous.

Silver halide emulsions suitable for rapid development preferably contain at least 90 mol-% of chloride, the remainder consisting of 0 to 10 mol-% bromide, iodide and thiocyanate, singly or in combination. The thiocyanate is regarded here as a substitute for halide (pseudohalide). These halides and pseudohalides are preferably used in the following quantities: From 0.01 to 0.5 mol-% of iodide, from 0.02 to 5 mol-% of bromide and from 0.02 to 5 mol-% of thiocyanate. The grain size varies from 0.3 to 0.9 μm, depending on the layer.

These substances may be predominantly compact crystals, e.g. they may have regular cubical or octahedral or transitional forms but may also advantageously include platelet shaped crystals having an average ratio of diameter to thickness of preferably not less than 5:1, the diameter of a grain being defined as the diameter of a circle having a surface area equal to the projected surface of the grain. The layers may also contain tabular silver halide crystals in which the ratio of diameter to thickness is substantially greater than 5:1, e.g. from 12:1 to 30:1.

The silver halide grains may also have a multilayered grain structure, in the simplest case comprising an inner and outer grain region (core/shell) which differ from one another in their halide composition and/or by other modifications, e.g. doping of the individual grain regions. The average grain size of the emulsions is preferably from 0.2 μm to 2.0 μm and the grain size distribution may be either homodisperse or heterodisperse. A homodisperse grain distribution means that 95% of the grains differ by not more than ±30% from the mean grain size. The emulsions may also contain organic silver salts in addition to silver halide, e.g. silver benzotriazolate or silver behenate.

Two or more types of silver halide emulsions which have been prepared separately may be used as a mixture.

The photographic emulsions may be prepared from soluble silver salts and soluble halides by various methods (e.g. P. Glafkides, Chimie et Physique Photographique, Paul Montel, Paris (1967), G. F. Duffin, Photographic Emulsion Chemistry, The Focal Press, London (1966), V. L. Zelikman et al, Making and Coating Photographic Emulsions, The Focal Press, London (1966)).

Precipitation of the silver halide is preferably carried out in the presence of the binder, e.g. gelatine, and may be carried out at an acid, neutral or alkaline pH, preferably with the addition of silver halide complex formers such as, for example, ammonia, thioethers, imidazole, ammonium thiocyanate or excess halide.

The water-soluble silver salts and the halides may be brought together selectively in succession by the single jet process or simultaneously by the double jet process or by any combination of these two processes. Dosing is preferably carried out at increasing inflow rates but the "critical" inflow rate at which new nuclei just fail to be formed should not be exceeded. The pAg range during precipitation may vary within wide limits; the so-called pAg controlled process is preferably employed, in which a certain pAg value is kept constant or the pAg passes through a particular profile during precipitation. Instead of the preferred method of precipitating with an excess of halide, so-called inverse precipitation with an excess of silver ions may be employed. The silver halide crystals may grow not only as a result of precipitation but also by physical ripening (Ostwald ripening) in the presence of excess halide and/or silver halide complex formers. Growth of the emulsion grains may indeed take place predominantly by Ostwald ripening in which a fine grained, so-called Lippmann emulsion is preferably mixed with a less readily soluble emulsion and dissolved and precipitated on the latter.

Salts or complexes of metals such as Cd, Zn, Pb, Tl, Bi, Ir, Rh or Fe may also be present during the precipitation and/or physical ripening of the silver halide grains.

Precipitation may also be carried out in the presence of sensitizing dyes. Complex formers and/or dyes may be rendered inactive at any stage, e.g. by altering the pH or by an oxidative treatment.

When crystal formation has been completed or at an earlier stage, the soluble salts are removed from the emulsion, e.g. by shredding and washing, by flocculation and washing, by ultrafiltration or by means of ion exchangers.

The silver halide emulsion is generally subjected to a chemical sensitization under specified conditions of pH, pAg, temperature and concentration of gelatine, silver halide and sensitizer until the optimum sensitivity and fog are obtained. The procedure is described, for example, in H. Frieser, "Die Grundlagen der Photographischen Prozesse mit Silberhalogeniden" pages 675–734, Akademische Verlagsgesellschaft (1968).

Chemical sensitization may be carried out with the addition of compounds of sulphur, selenium or tellurium and/or compounds of the metals of sub-Group VIII of the Periodic System (e.g. gold, platinum, palladium, iridium), and thiocyanate compounds, surface active compounds such as thioethers, heterocyclic nitrogen compounds (e.g. imidazoles, azaindenes) and spectral sensitizers may also be added (described e.g. in F. Hamer, "The Cyanine Dyes and Related Compounds", 1964, and Ullmanns Encyclopädie der technischen Chemie, 4th Edition, Volume 18, pages 431 et seq and Research Disclosure 17643 (December 1978), Chapter III. A reduction sensitization may be carried out instead of or in addition to the chemical sensitization by adding reducing agents (tin-II salts, amines, hydrazine derivatives, aminoboranes, silanes, formamidine sulphinic acid) or by means of hydrogen or by employing a low pAg (e.g. below 5) and/or a high pH (e.g. above 8).

The photographic emulsions may contain compounds for preventing fogging or for stabilizing the photographic function during production, storage and photographic processing.

Azaindenes are particularly suitable, preferably tetra- and pentaazaindenes, in particular those which are substituted with hydroxyl or amino groups. Such compounds are described e.g. by Birr in Z. Wiss. Phot. 47 (1952), pages 2–58. Salts of metals such as mercury or cadmium, aromatic sulphonic or sulphinic acids such as benzene sulphinic acid, nitrogen-containing heterocyclic compounds such as nitrobenzimidazole or nitroindazole, and substituted or unsubstituted benzotriazoles or benzothiazolium salts may also be used as antifoggants. Heterocyclic compounds containing mercapto groups are particularly suitable, e.g. mercaptobenzothiazoles, mercaptobenzimidazoles, mercaptotetrazoles, mercaptothiadiazoles or mercaptopyrimidines. These mercaptoazoles may also contain a group which renders them water soluble, e.g. a carboxyl group or a sulpho group. Other suitable compounds are disclosed in Research Disclosure 17643 (December 1978), Chapter VI.

The stabilizers may be added to the silver halide emulsions before, during or after ripening. The compounds may, of course, also be added to other photographic layers which are associated with a silver halide layer.

Mixtures of two or more of the above-mentioned compounds may also be used.

The photographic emulsion layers or other hydrophilic colloid layers of the light sensitive material prepared according to the invention may contain surface-active agents for various purposes, such as coating auxiliaries and agents for preventing electric charging, for improving the slip properties, for emulsifying the dispersion, for preventing adherence and for improving the photographic characteristics (e.g. development acceleration, high contrast, sensitization, etc.). Apart from naturally occurring surface active compounds such as saponin, synthetic surface-active compounds (surfactants) are mainly used: Non-ionic surfactants, e.g. alkylene oxide compounds, glycerol compounds or glycidol compounds; cationic surfactants, e.g. higher alkylamines, quaternary ammonium salts, pyridine compounds and other heterocyclic compounds, sulphonium compounds or phosphonium compounds; anionic surfactants containing an acid group, e.g. a carboxylic acid, sulphonic acid, phosphoric acid, sulphuric acid ester or phosphoric acid ester group, ampholytic surfactants, e.g. amino acid and amino sulphonic acid compounds, and sulphuric or phosphoric acid esters of an amino alcohol.

The photographic emulsions may be spectrally sensitized by means of methine dyes or other dyes. Cyanine dyes, merocyanine dyes and complex merocyanine dyes are particularly suitable.

A survey of polymethine dyes suitable as spectral sensitizers, suitable combinations thereof and combinations which have a supersensitizing action is contained in Research Disclosure 17643 (December 1978) Chapter IV.

The following dyes in particular are suitable, given in the order of their spectral regions:

1. as red sensitizers

9-Ethylcarbocyanines having benzothiazole, benzoselenazole or naphthothiazole as basic end groups which may be substituted in the 5- and/or 6-position by halogen, methyl, methoxy, carbalkoxy or aryl; and 9-ethyl-naphthoxathia- or -selenocarbocyanines and 9-ethyl-naphthothiaoxa- or -benzimidazocarbocyanines, provided the dyes carry at least one sulphoalkyl group on the heterocyclic nitrogen.

2. as green sensitizers

9-Ethylcarbocyanines having benzoxazole, naphthoxazole or a benzoxazole and a benzothiazole as basic end groups; and benzimidazocarbocyanines which may be further substituted and must also carry at least one sulphoalkyl group on the heterocyclic nitrogen.

3. as blue sensitizers

Symmetric or asymmetric benzimidazo-, oxa-, thia- or selenocyanines having at least one sulphoalkyl group on the heterocyclic nitrogen and optionally further substituents on the aromatic nucleus; and apomerocyanines containing a rhodanine group.

Sensitizers may be omitted if the intrinsic sensitivity of the silver halide is sufficient for a particular spectral region, for example the blue sensitivity of silver bromides.

Non-diffusible, low molecular weight or polymeric colour couplers are associated with the various emulsion layers which have been sensitized to different regions of the spectrum. These colour couplers may be situated in the same layer with which they are associated or in an adjacent layer. Cyan couplers are normally associated with the red sensitive layers, magenta couplers with the green sensitive layers and yellow couplers with the blue sensitive layers.

The colour couplers may be 4-equivalent couplers or 2-equivalent couplers. The latter are derived from 4-equivalent couplers in that they carry in the coupling position a substituent which is split off in the formation of the dye.

The following are examples of suitable cyan couplers:

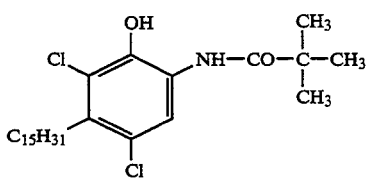

C-1

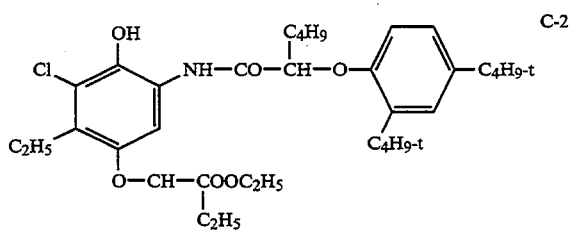

C-2

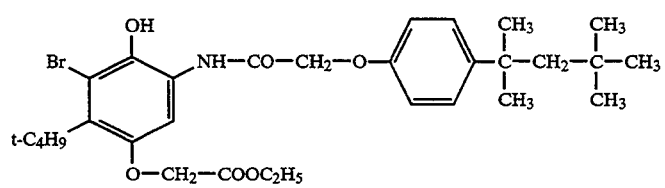

C-3

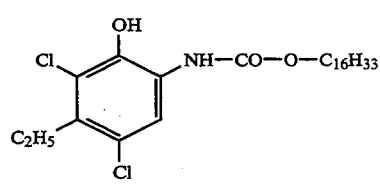

C-4

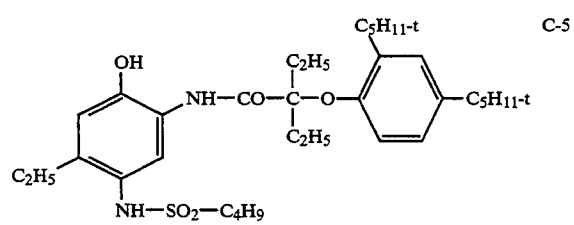

C-5

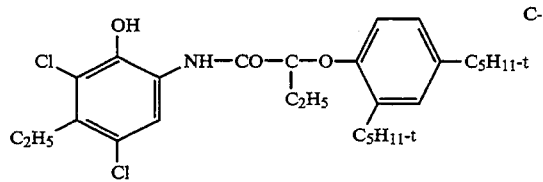
C-6
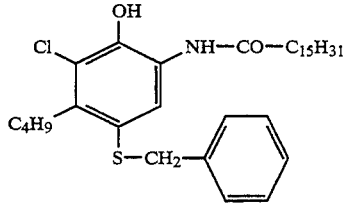
C-7
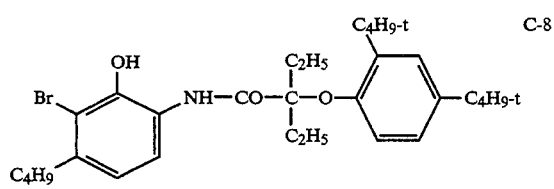
C-8
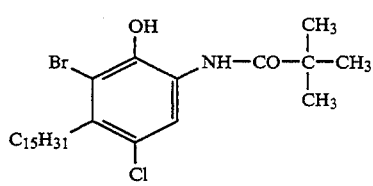
C-9
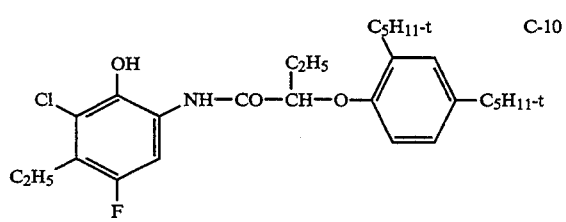
C-10
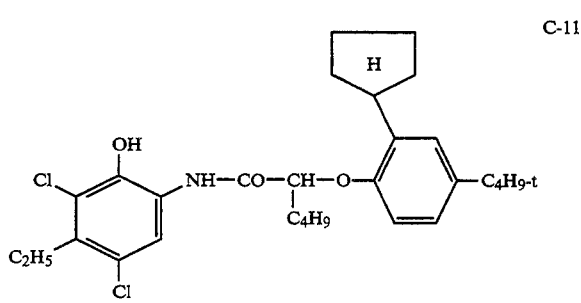
C-11
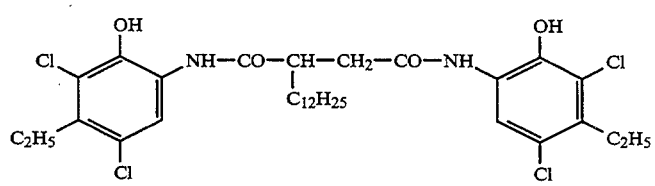
C-12
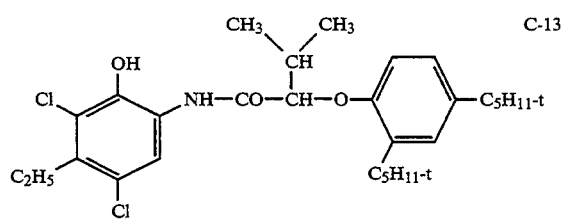
C-13
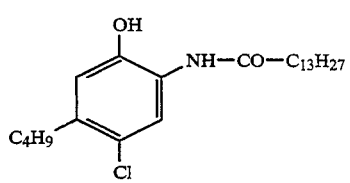
C-14
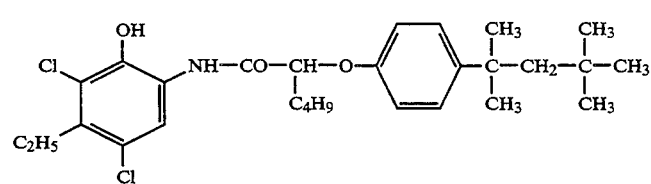
C-15
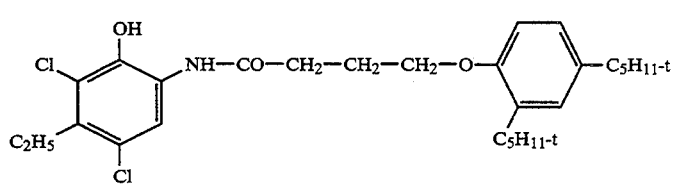
C-16
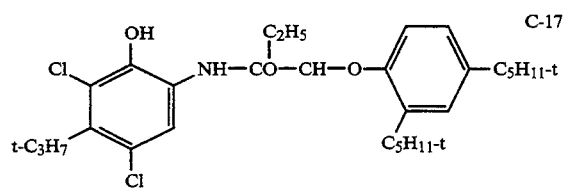
C-17
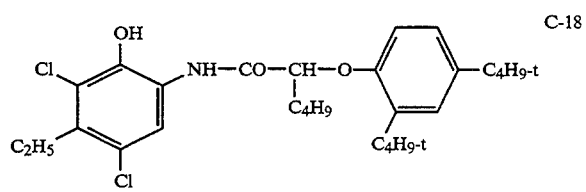
C-18

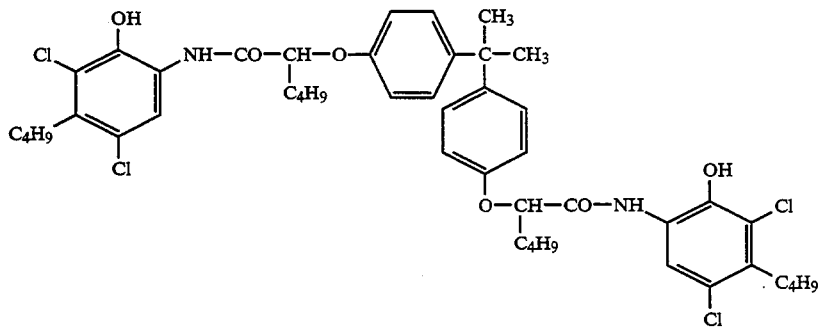
C-19
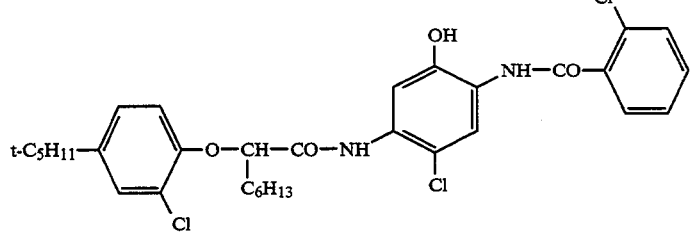
C-20
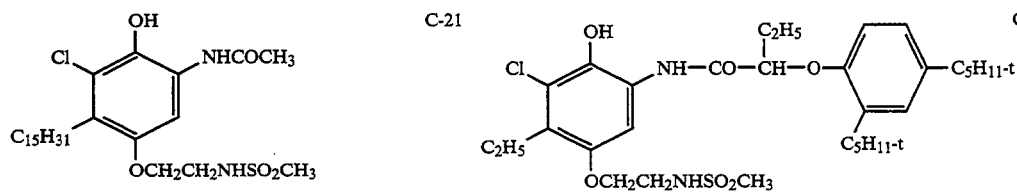
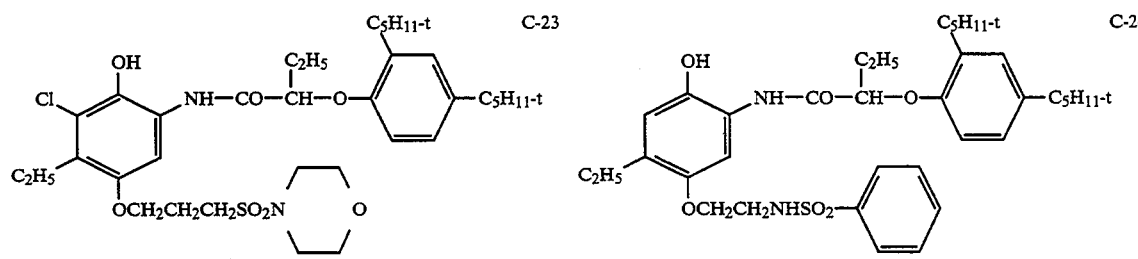
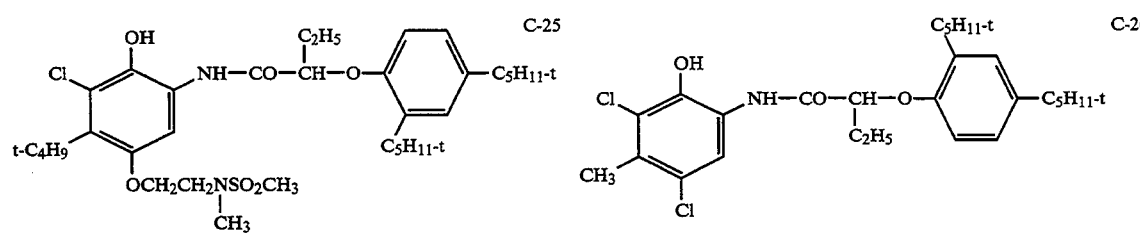
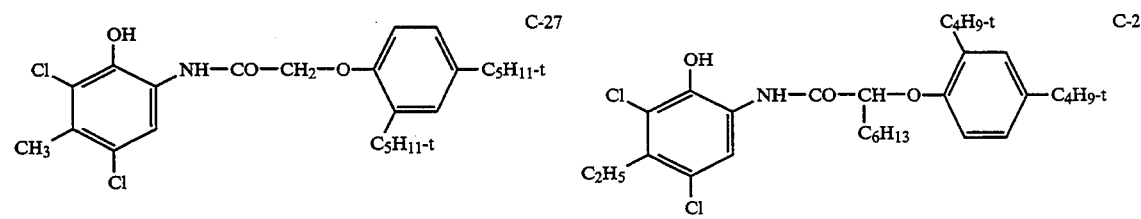
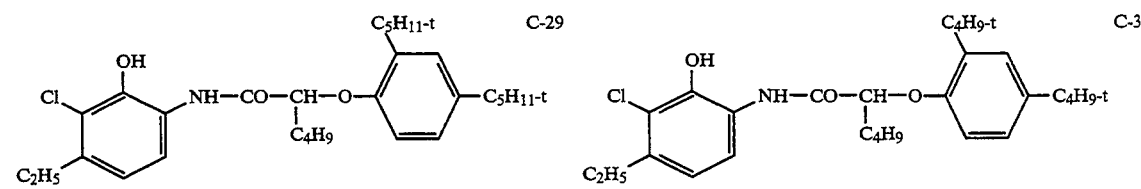

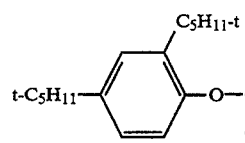 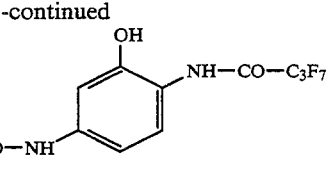
C-31
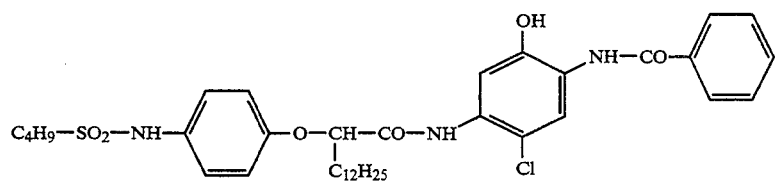
C-32
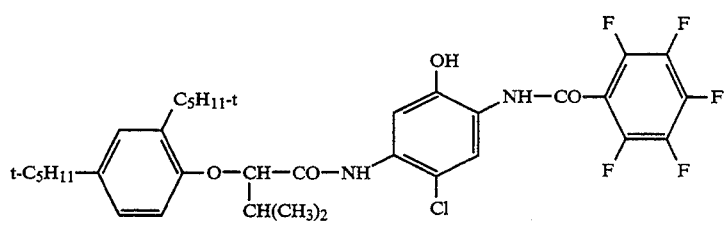
C-33
Magenta couplers of the 5-pyrazolone series and the pyrazoloazole series are generally suitable as colour couplers for producing the magenta partial colour image; the following are examples of these:
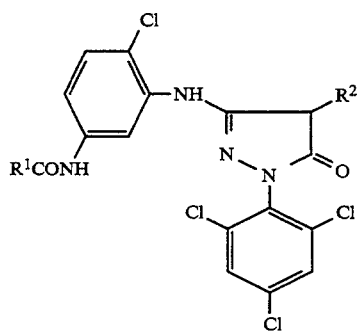
M-1:
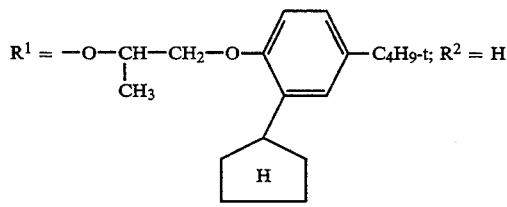
M-2:
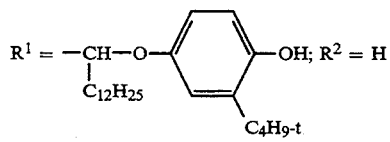
M-3:
$R^1 = -C_{13}H_{27}; R^2 = H$
M-4:
$R^1 = -OC_{16}H_{33}; R^2 = H$
M-5:

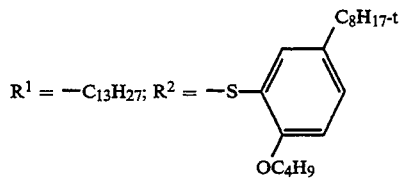
M-6:
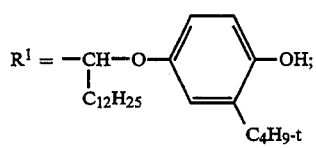
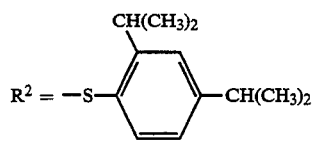
M-7:
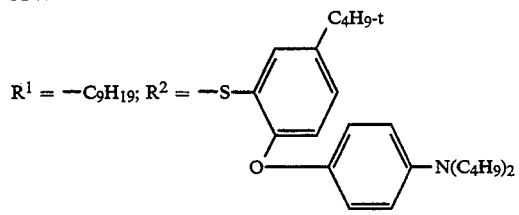
M-8:
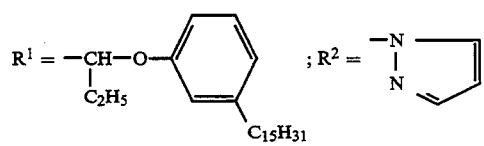
M-9:
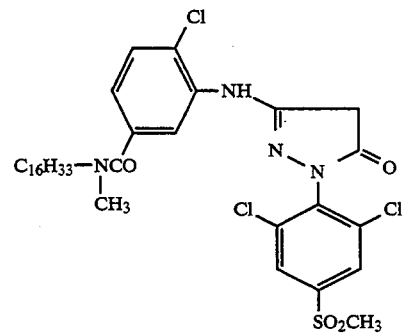
M-10:
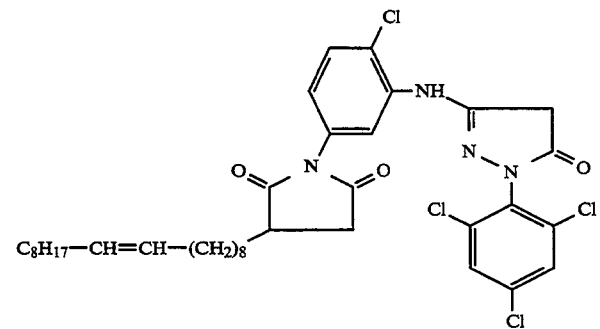

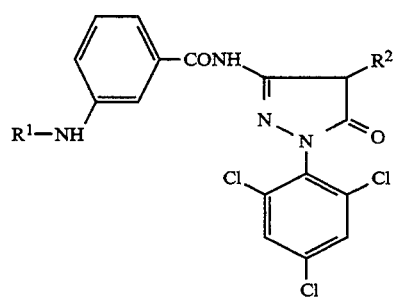
M-11:
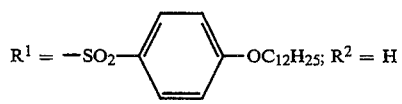
M-12:
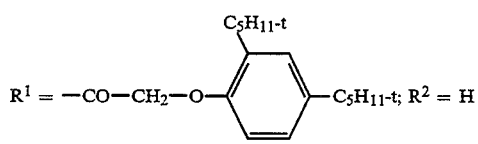
M-13:
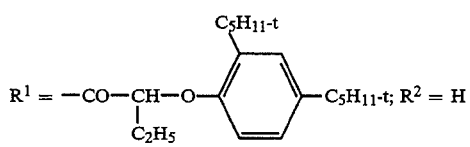
M-14:
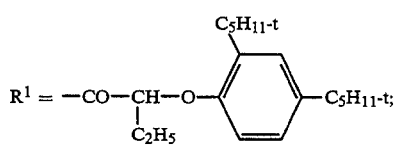
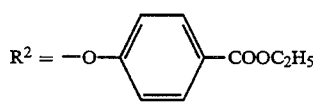
M-15:
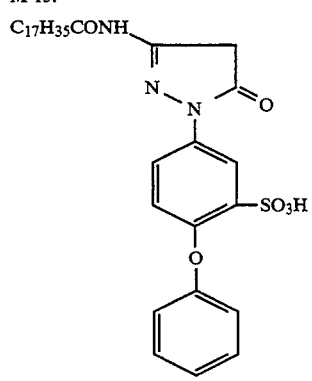
M-16:

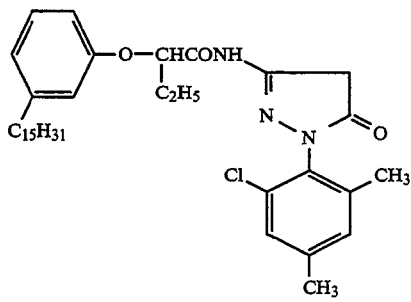
M-17:
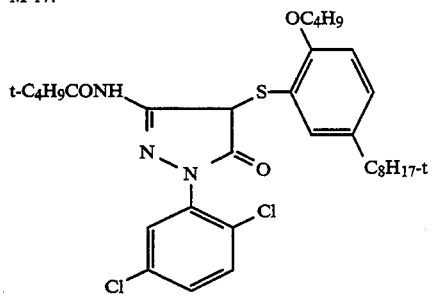
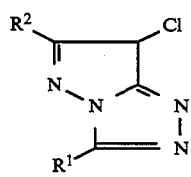
M-18:
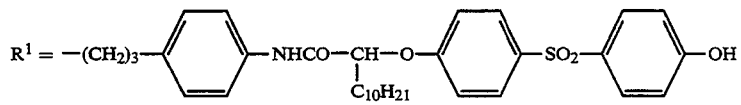
$R^2 = -CH_3$
M-19:
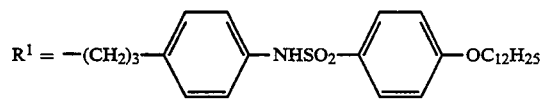
$R^2 = -CH_3$
M-20:
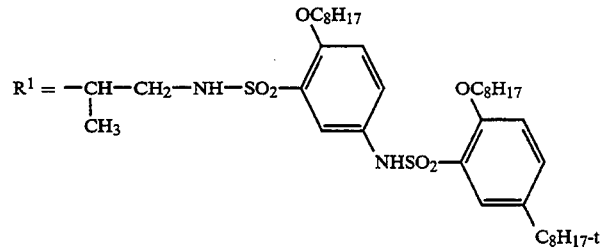
$R^2 = -C_4H_9\text{-}t$
M-21:
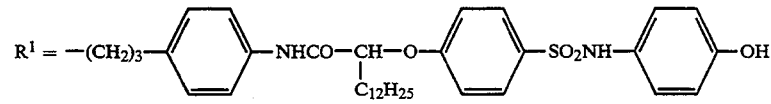
$R^2 = -CH_3$ M-22:
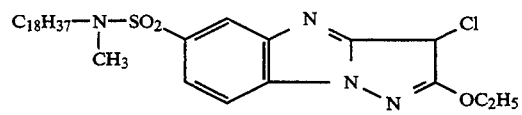
Colour couplers for producing the yellow partial colour image are generally couplers carrying an open chain ketomethylene group, in particular couplers of the α-acylacetamide series; α-benzoylacetanilide couplers and α-pivaloyl acetanilide couplers corresponding to the following formulae are suitable examples of these:
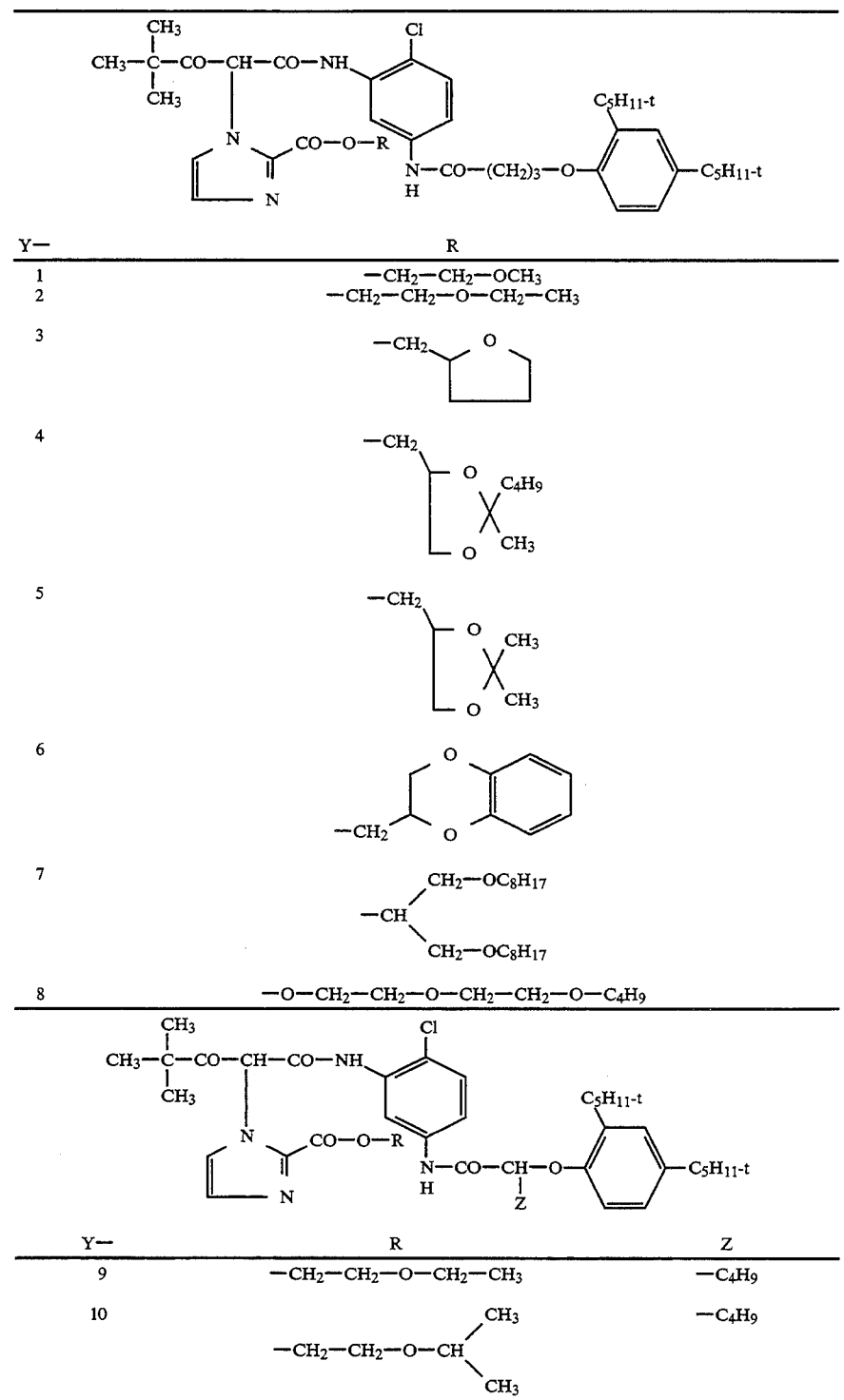

-continued
| | | |
|---|---|---|
| 11 | 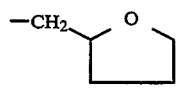 | —C₄H₉ |
| 12 | —CH₂—CH₂—OC₂H₅ | —C₂H₅ |
| 13 | 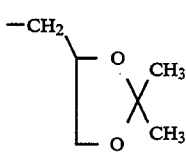 | —C₂H₅ |
| 14 | 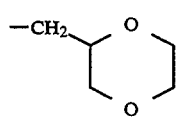 | —C₂H₅ |
| 15 | —CH₂—CH₂—OC₂H₅ | H |
| 16 | 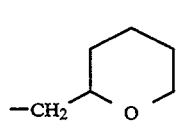 | H |
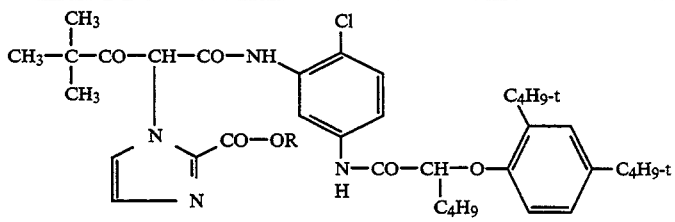
| Y— | R |
|---|---|
| 17 | —CH₂—CH₂—OCH₃ |
| 18 | 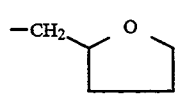 |
| 19 | 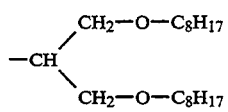 |
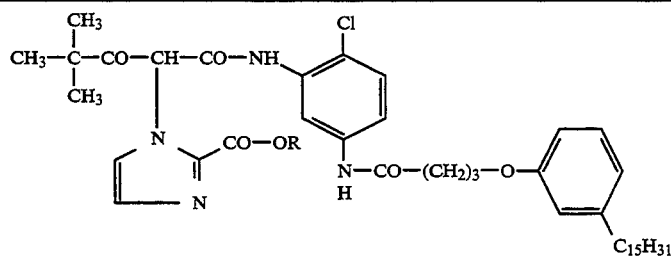
| Y— | R |
|---|---|
| 20 | —CH₂—CH₂—OC₂H₅ |
| 21 | 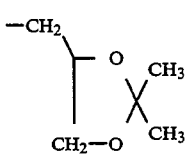 |

-continued
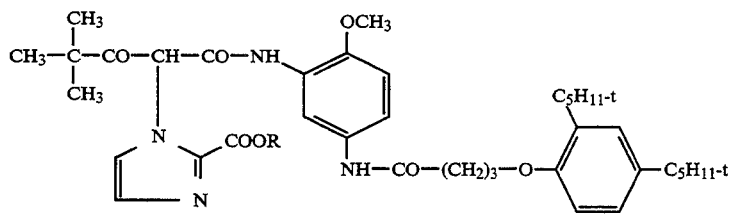
| Y— | R |
|---|---|
| 22 | —CH$_2$—CH$_2$—OCH$_3$ |
| 23 | —CH$_2$—CH$_2$—OCH$_2$—CH$_2$—OC$_4$H$_9$ |
| 24 | 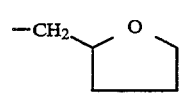 |
| 25 | 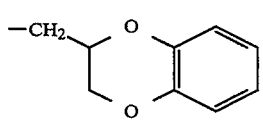 |
| 26 | 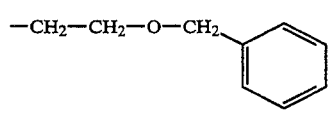 |
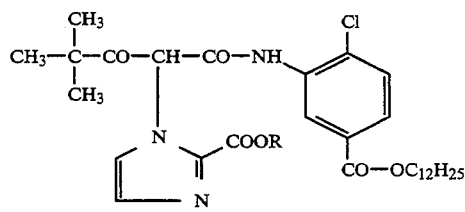
| Y— | R |
|---|---|
| 27 | —CH$_2$—CH$_2$—OCH$_3$ |
| 28 | —CH$_2$—CH$_2$—O—CH$_2$—CH$_2$—O—C$_2$H$_5$ |
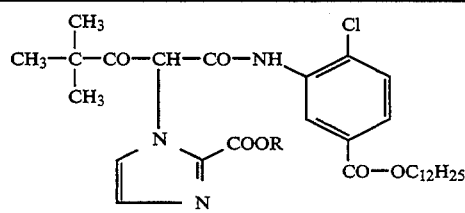
| Y— | R |
|---|---|
| 29 | 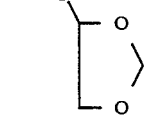 |
| 30 | 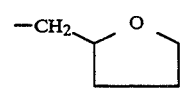 |
| 31 | 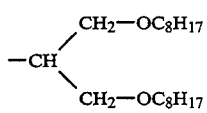 |

-continued
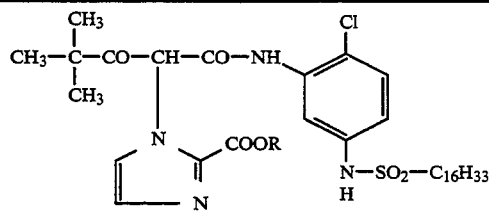
| Y— | R |
|---|---|
| 32 | —CH$_2$—CH$_2$—OCH$_3$ |
| 33 |  |
| Y— | R |
|---|---|
| 34 | 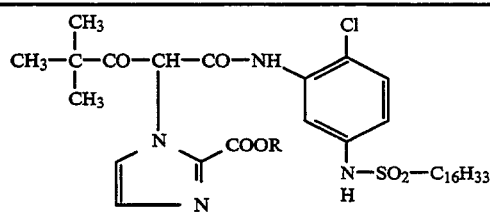 |
| 35 | 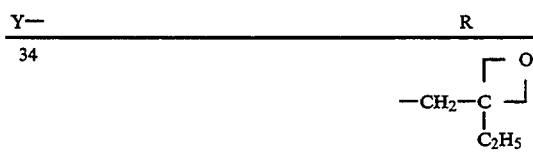 |
| Y— | R |
|---|---|
| 36 | —CH$_2$—CH$_2$—OCH$_3$ |
| 37 | —CH$_2$—CH$_2$—OC$_2$H$_5$ |
| 38 | 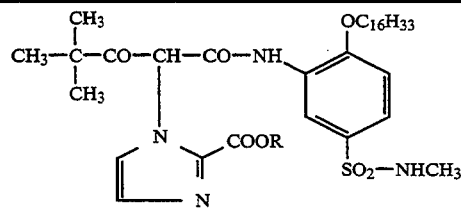 |
| 39 | 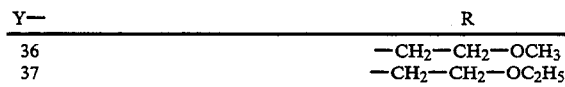 |

-continued
| Y— | R |
|---|---|
| 40 | 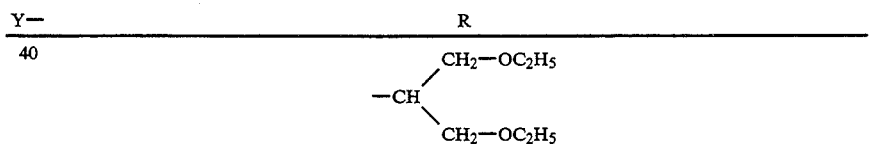 |
| 41 |  |
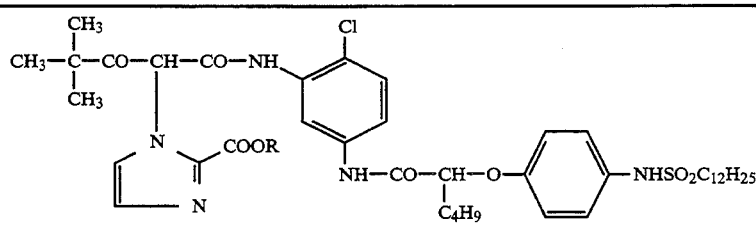
| Y— | R |
|---|---|
| 42 | —CH$_2$—CH$_2$—OC$_2$H$_5$ |
| 43 | —CH$_2$—CH$_2$—O—CH$_2$—CH$_2$—OC$_2$H$_5$ |
| 44 |  |
| 45 |  |
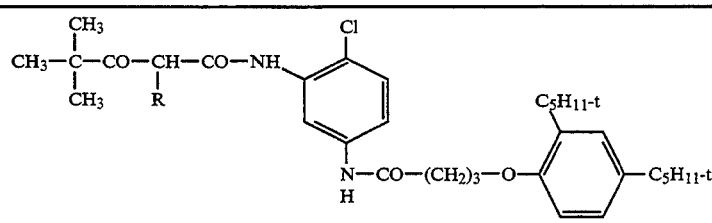
| Y— | R |
|---|---|
| 46 | 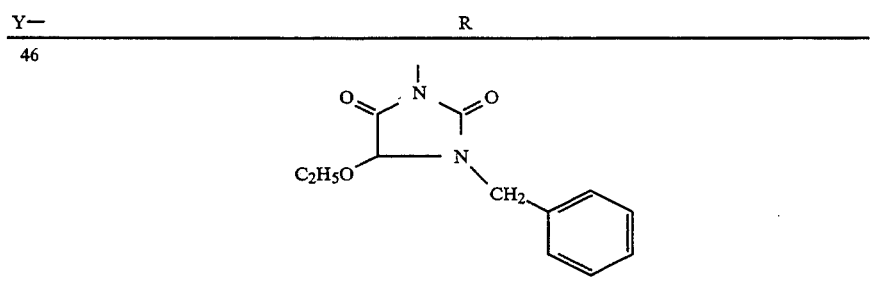 |
| 47 |  |
| 48 |  |

-continued
49
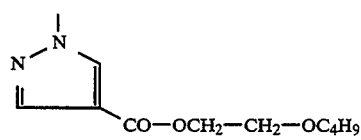
50
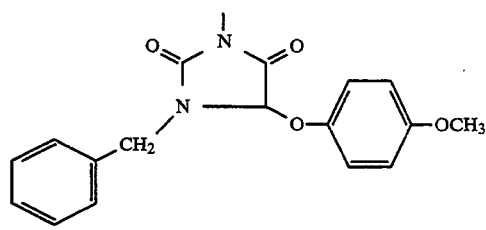
51
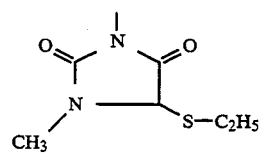
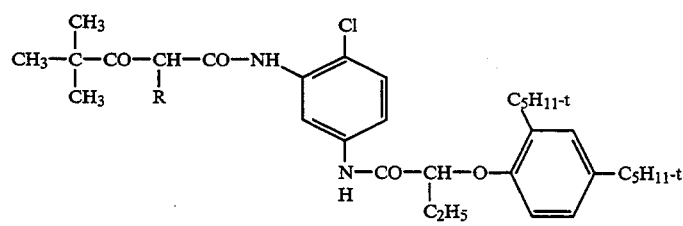
| Y— | R |
|---|---|
| 52 | 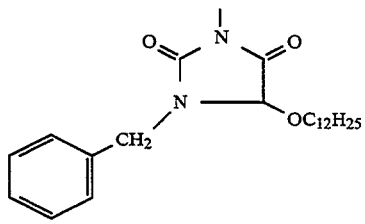 |
| 53 | 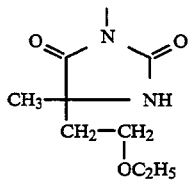 |
| 54 | 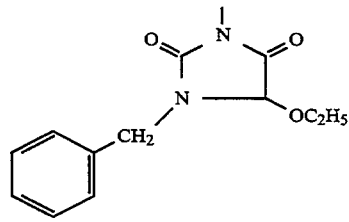 |

-continued
55
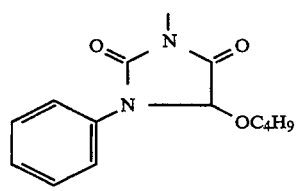
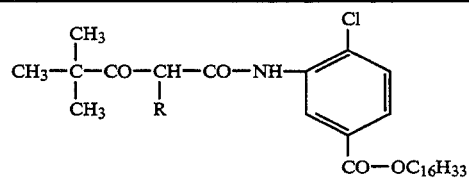
| Y— | R |
|---|---|
| 56 | 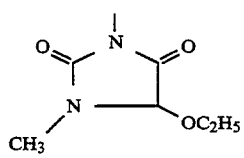 |
| 57 | 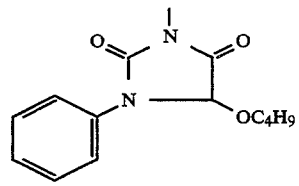 |
| 58 | 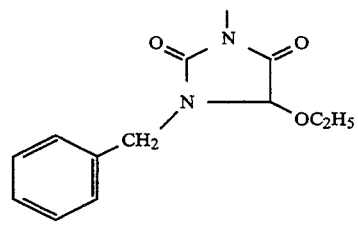 |
| 59 | 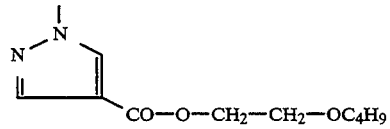 |
| 60 | 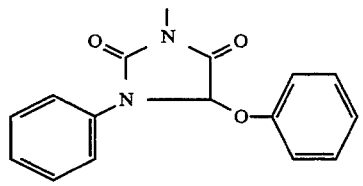 |
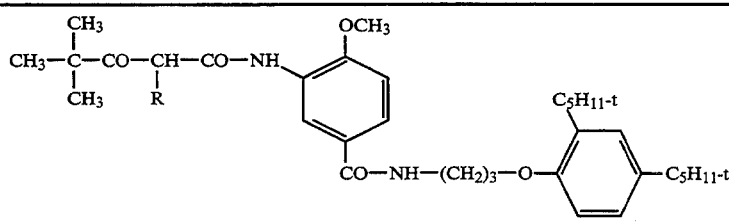
| Y— | R |
|---|---|

| | |
|---|---|
| 61 | 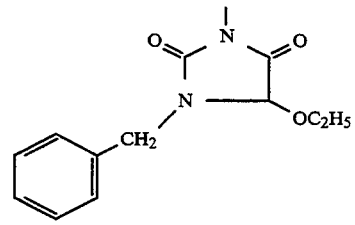 |
| 62 | 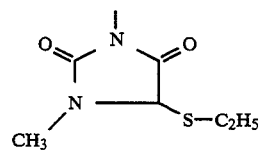 |
| | 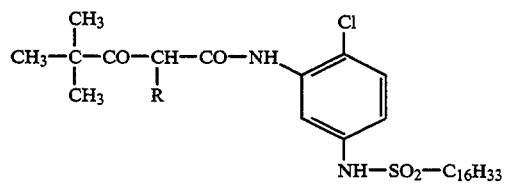 |
| 63 | 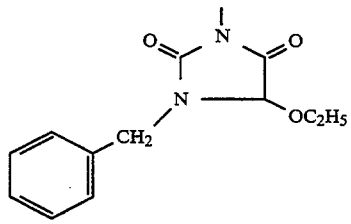 |
| 64 | 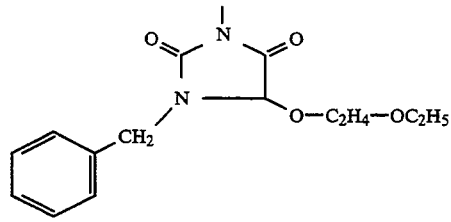 |
| 65 | 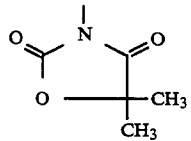 |
| | 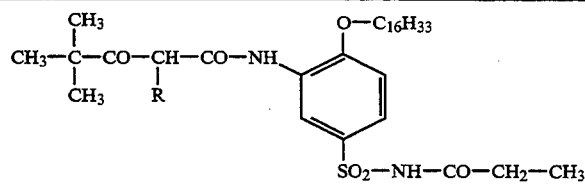 |
| Y— | R |
|---|---|
| 66 | 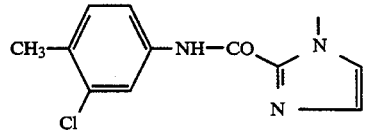 |

-continued
| 67 | 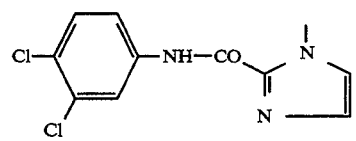 |
| 68 | 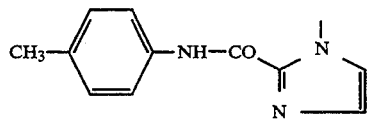 |
| 69 | 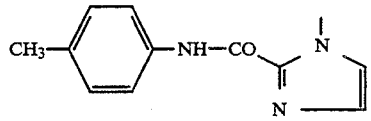 |
| 70 | 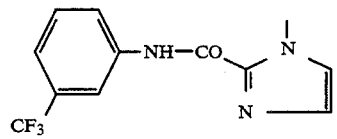 |
| 71 | 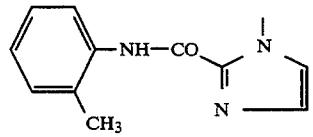 |
| 72 | 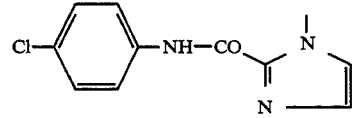 |
| 73 | 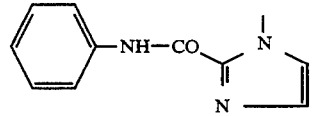 |
| 74 | 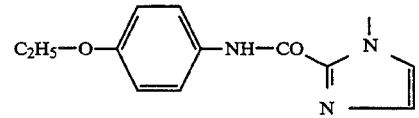 |
| 75 | 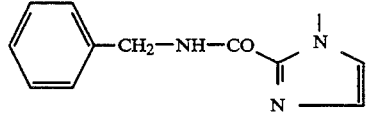 |
| 76 | 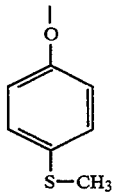 |

-continued
77 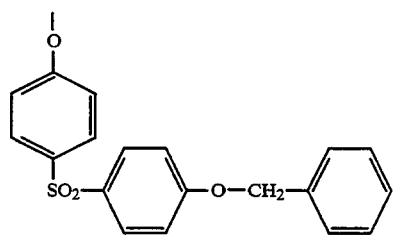
78 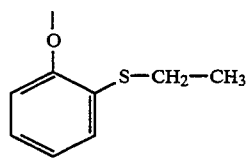
79 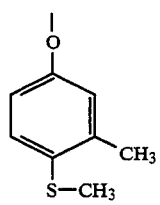
80 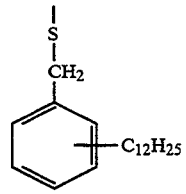
81 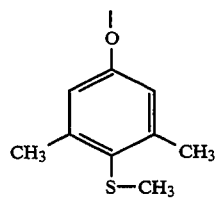
82 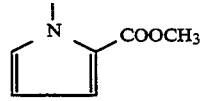
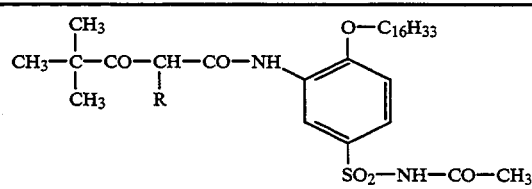
| Y— | R |
|---|---|
| 83 | 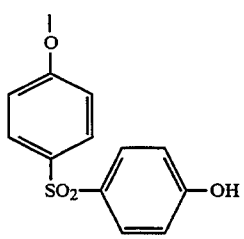 |

84 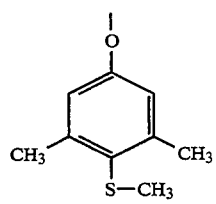
85 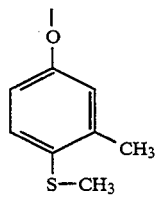
86 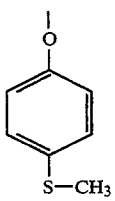
87 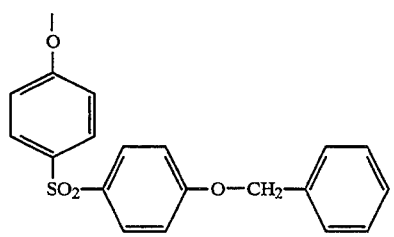
88 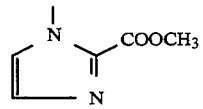
89 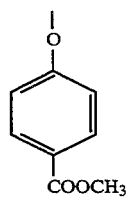
90 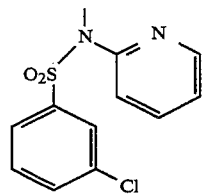
91 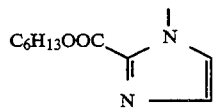

|   |   |
|---|---|
| 92 | 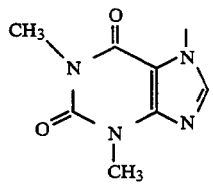 |
| 93 | 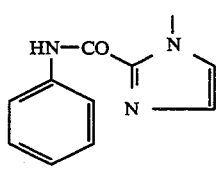 |
| 94 | 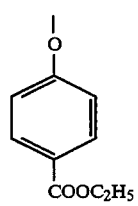 |
| 95 | 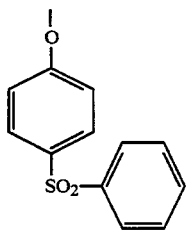 |
|   | 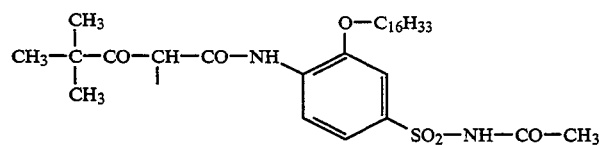 |
| Y— | R |
| 96 | 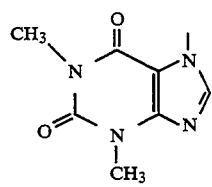 |
| 97 | 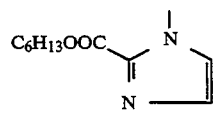 |
| 98 | 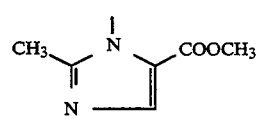 |

-continued
99
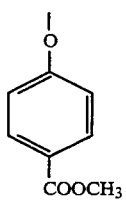
100
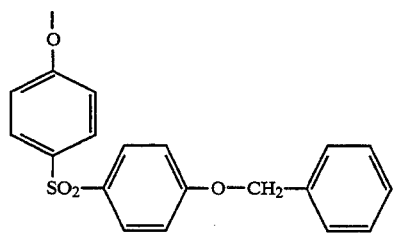
Y-106
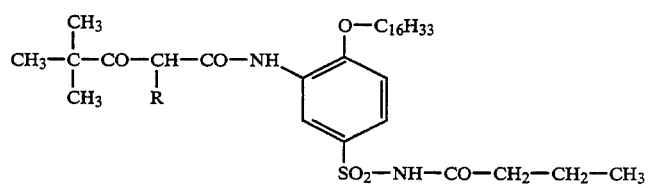
| Y— | R |
|---|---|
| 101 | 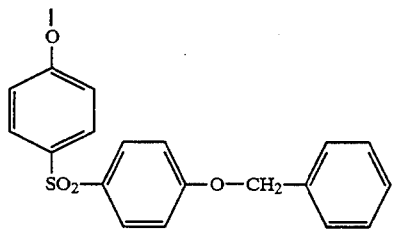 |
| 102 | 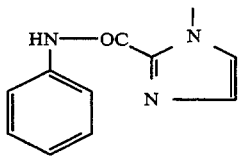 |
| 103 | 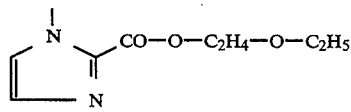 |
| 104 | 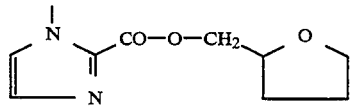 |
| 105 | 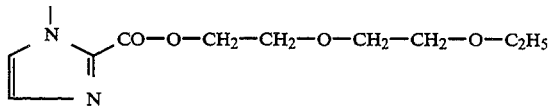 |

106
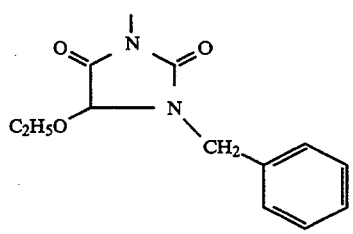

107
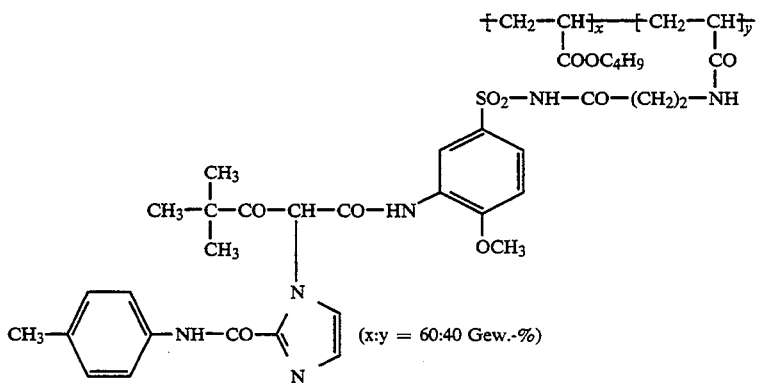

108
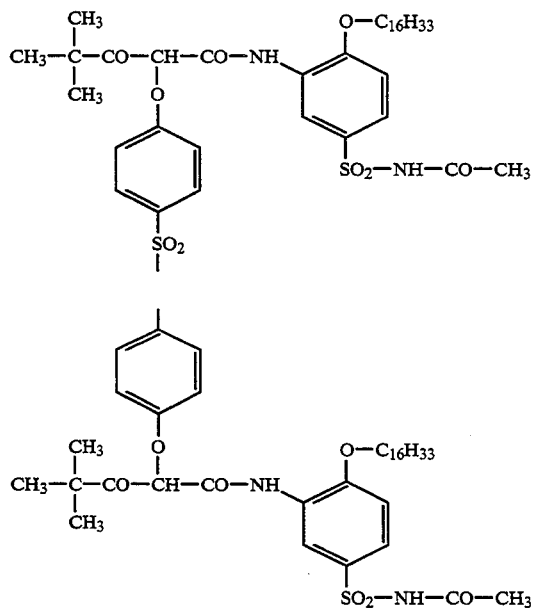

High molecular weight colour couplers are described, for example, in DE-C-1 297 417, DE-A-24 07 569, DE-A-31 48 125, DE-A-32 17 200, DE-A-33 20 079, DE-A-33 24 932, DE-A-33 31 743, DE-A-33 40 376, EP-A-27 284 and U.S. Pat. No. 4,080,211. The high molecular weight colour couplers are generally prepared by the polymerisation of ethylenically unsaturated monomeric colour couplers but they may also be obtained by polyaddition or polycondensation.

Incorporation of the couplers or other compounds in silver halide emulsion layers may be carried out by first preparing a solution, dispersion or emulsion of the particular compound and then adding this to the casting solution for the particular layer. The choice of suitable solvent or dispersing agent depends on the solubility of the compound.

Grinding processes for introducing compounds which are substantially insoluble in water are described, for example, in DE-A-26 09 741 and DE-A-26 09 742.

Hydrophobic compounds may also be introduced into the casting solution by means of high boiling solvents, so-called oil formers. Suitable methods are described, for example, in U.S. Pat. No. 2,322,027, U.S. Pat. No. 2,801,170, U.S. Pat. No. 2,801,171 and EP-A-0 043 037.

Oligomeric or polymeric, so-called polymeric oil formers may be used instead of high boiling solvents.

The compounds may also be introduced into the casting solution in the form of charged latices; see, for example, DE-A-25 41 230, DE-A-25 41 274, DE-A-28 35 856, EP-A-0 014 921, EP-A-0 069 671, EP-A-0 130 115 and U.S. Pat. No. 4,291,113.

Suitable oil formers are, for example, the following: Phthalic acid alkyl esters, phosphonic acid esters, phosphoric acid esters, citric acid esters, benzoic acid esters, amides, fatty acid esters, trimesic acid esters, alcohols, phenols, aniline derivatives and hydrocarbons.

The following are specific examples of suitable oil formers:

Dibutylphthalate, dicyclohexylphthalate, di-2-ethylhexylphthalate, decylphthalate, triphenyl phosphate, tricresyl phosphate, 2-ethylhexyl diphenylphosphate, tricyclohexylphosphate, tri-2-ethylhexylphosphate, tridecylphosphate, tributoxyethylphosphate, trichloropropylphosphate, di-2-ethylhexylphenylphosphate, 2-ethylhexylbenzoate, dodecylbenzoate, 2-ethylhexyl-p-hydroxybenzoate, diethyldodecanamide, N-tetradecylpyrrolidone, isostearyl alcohol, 2,4-di-t-amylphenol, dioctylacetate, glycerol tributyrate, isostearyl lactate, trioctyl citrate, N,N-dibutyl-2-butoxy-5-t-octylaniline, paraffin, dodecylbenzene and diisopropylnaphthalene.

The light insensitive interlayers generally arranged between layers differing in spectral sensitivity may contain agents which prevent unwanted diffusion of developer oxidation products from one light sensitive layer into another light sensitive layer of a different spectral sensitization.

The photographic material may also contain UV light absorbent compounds, white toners, spacers, filter dyes, light protective agents, antioxidants, $D_{min}$ dyes, additives for improving the stabilization of the dyes, couplers and whites and for reducing the colour fog, plasticizers (latices), biocidal agents and others.

UV Light absorbent compounds should on the one hand protect the image dyes against bleaching by daylight rich in UV light and on the other hand act as filter dyes to absorb the UV light present in daylight when exposure is carried out and thus improve the colour reproduction of the film. Compounds of different structures are normally used for the two different problems. Examples include aryl substituted benzotriazole compounds (U.S. Pat. No. 3,533,794), 4-thiazolidone compounds (U.S. Pat. No. 3,314,794 and 3,352,681), benzophenone compounds (JP-A-2784/71), cinnamic acid ester compounds (U.S. Pat. No. 3,705,805 and 3,707,375), butadiene compounds (U.S. Pat. No. 4,045,229) and benzoxazole compounds (U.S. Pat. No. 3,700,455).

The following are examples of particularly suitable compounds:

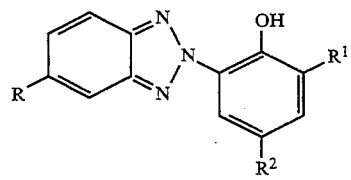

$R, R^1 = H; R^2 = -C_4H_9\text{-}t$
$R = H; R^1, R^2 = -C_4H_9\text{-}t$
$R = H; R^1, R^2 = -C_5H_{11}\text{-}t$
$R = H; R^1 = -C_4H_9\text{-}s; R^2 = -C_4H_9\text{-}t$
$R = Cl; R^1 = -C_4H_9\text{-}t; R^2 = -C_4H_9\text{-}s$
$R = Cl; R^1, R^2 = -C_4H_9\text{-}t$
$R = Cl; R^1 = -C_4H_9\text{-}t; R^2 = -CH_2-CH_2-COOC_8H_{17}$
$R = H; R = -C_{12}H_{25}\text{-}i; R^2 = -CH_3$
$R, R^1, R^2 = -C_4H_9\text{-}t$

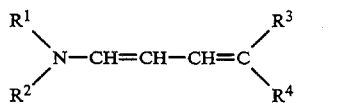

$R^1, R^2 = -C_6H_{13}\text{-}n; R^3, R^4 = -CN$

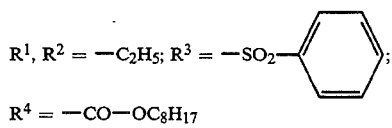

$R^1, R^2 = -C_2H_5; R^3 = -SO_2-\phi;$
$R^4 = -CO-OC_8H_{17}$

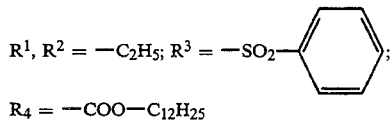

$R^1, R^2 = -C_2H_5; R^3 = -SO_2-\phi;$
$R_4 = -COO-C_{12}H_{25}$ $R^1, R^2 = -CH_2-CH=CH_2; R^3, R^4 = -CN$

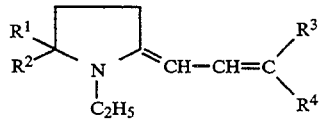

-continued

R¹, R² = H;   R³ = —CN;   R⁴ = —CO—NHC₁₂H₂₅
R¹, R² = —CH₃;   R³ = —CN;   R⁴ = —CO—NHC₁₂H₂₅

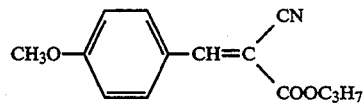

Suitable white toners are described, for example, in Research Disclosure 17 643 (December 1978), Chapter V, in U.S. Pat. No. 2,632,701 and 3,269,840 and in GB-A-852 075 and 1 319 763.

Certain layers of binders, in particular those furthest removed from the support but occasionally also interlayers, especially if they were the layers furthest from the support during the preparation, may contain photographically inert particles of an inorganic or organic nature, e.g. as matting agents or as spacers (DE-A-33 31 542, DE-A-34 24 893, and Research Disclosure 17 643 (December 1978), Chapter XVI).

The mean particle diameter of the spacers is in particular in the range of from 0.2 to 10 μm. The spacers are insoluble in water and may be soluble or insoluble in alkalies; those which are soluble in alkalies are generally removed from the photographic material in the alkaline development bath. The following are examples of suitable polymers: Polymethyl methacrylate, copolymers of acrylic acid and methyl methacrylate and hydroxypropyl methyl cellulose hexahydrophthalate.

Additives for improving the stability of the dyes, couplers and whites and for reducing the colour fog (Research Disclosure 17 643 (December 1978), Chapter VII) may belong to the following classes of chemical substances: Hydroquinones, 6-hydroxychromans, 5-hydroxycoumarans, spirochromans, spiroindanes, p-alkoxyphenols, sterically hindered phenols, gallic acid derivatives, methylene dioxybenzenes, aminophenols, sterically hindered amines, derivatives having esterified or etherified phenolic hydroxyl groups, and metal complexes.

Compounds having both a sterically hindered amine partial structure and a sterically hindered phenol partial structure in one molecule (U.S. Pat. No. 4,268,593) are particularly effective in preventing any impairment of the yellow dye images as a result of heat, moisture and light. Spiroindans (JP-A-159 644/81) and chromans substituted by hydroquinone diethers or monoethers (JP-A-89 835/80) are particularly effective in preventing impairment to magenta colour images, especially impairment due to the action of light.

The layers of the photographic material may be hardened with conventional hardeners. Examples of suitable hardeners are: Formaldehyde, glutaraldehyde and similar aldehyde compounds, diacetyl, cyclopentadione and similar ketone compounds, bis-(2-chloroethylurea), 2-hydroxy-4,6-dichloro-1,3,5-triazine and other compounds which contain reactive halogen (U.S. Pat. No. 3,288,775, U.S. Pat. No. 2,732,303, GB-A-974 723 and GB-A-1 167 207), divinylsulphone compounds, 5-acetyl-1,3-diacryloylhexahydro-1,3,5-triazine and other compounds containing a reactive olefin bond (U.S. Pat. No. 3,635,718, U.S. Pat. No. 3,232,763 and GB-A-994 869); N-hydroxymethylphthalimide and other N-methylol compounds (U.S. Pat. No. 2,732,316 and U.S. Pat. No. 2,586,168); isocyanates (U.S. Pat. No. 3,103,437); aziridine compounds (U.S. Pat. No. 3,017,280 and U.S. Pat. No. 2,983,611); acid derivatives (U.S. Pat. No. 2,725,294 and U.S. Pat. No. 2,725,295); compounds of the carbodiimide series (U.S. Pat. No. 3,100,704); carbamoyl pyridinium salts (DE-A-22 25 230 and DE-A-24 39 551); carbamoyloxypyridinium compounds (DE-A-24 08 814); compounds containing a phosphorus-halogen bond (JP-A-113 929/83); N-carbonyloximide compounds (JP-A-43353/81); N-sulphonyloximido compounds (U.S. Pat. No. 4,111,926), dihydroquinoline compounds (U.S. Pat. No. 4,013,468), 2-sulphonyloxypyridinium salts (JP-A-110 762/81), formamidinium salts (EP-A-0 162 308), compounds having two or more N-acyloximino groups (U.S. Pat. No. 4,052,373), epoxy compounds (U.S. Pat. No. 3,091,537), compounds of the isoxazole series (U.S. Pat. No. 3,321,313 and U.S. Pat No. 3,543,292); halogenocarboxyaldehydes such as mucochloric acid; dioxane derivatives such as dihydroxydioxane and dichlorodioxane; and inorganic hardeners such as chrome alum and zirconium sulphate.

Hardening may be brought about in known manner by adding the hardener to the casting solution for the layer which is to be hardened or by coating the layer to be hardened with a layer containing a diffusible hardener.

The classes mentioned above include slow acting hardeners and quick acting hardeners and so-called instant hardeners, which are particularly advantageous. Instant hardeners are compounds which cross-link suitable binders to such a degree immediately after casting but at latest after 24 hours and preferably after not more than 8 hours that no further change in sensitometry and swelling of the combination of layers is brought about by the cross-linking reaction. By swelling is meant the difference between the wet layer thickness and the dry layer thickness when a film is processed under aqueous conditions (Photographic Sci. Eng. 8 (1964), 275; Photographic Sci. Eng, (1972), 449).

Examples of these hardeners which react very rapidly with gelatine include carbamoylpyridinium salts, which are capable of reacting with the free carboxyl groups of gelatine so that these react with free amino groups of gelatine to form peptide bonds and bring about the cross-linking of gelatine.

Examples of suitable instant hardeners include compounds corresponding to the following general formulae:

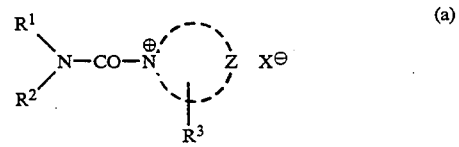

(a)

wherein
R¹ denotes alkyl, aryl or aralkyl, $R^2$ has the same meaning as $R^1$ or denotes alkylene, arylene, aralkylene or alkaralkylene in which the second bond is attached to a group of the following formula:

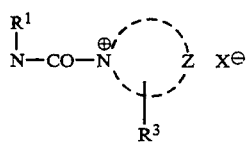

$R^1$ and $R^2$ together denote the atoms required for completing an optionally substituted heterocyclic ring, for example a piperidine, piperazine or morpholine ring, which rings may be substituted, e.g. by $C_1-C_3$-alkyl or by halogen, $R^3$ denotes hydrogen, alkyl, aryl, alkoxy, $NR^4COR^5$, $(CH_2)_m-NR^8R^9$, $(CH_2)_n-CONR^{13}R^{14}$ or

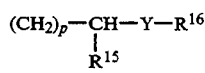

or a bridging member or a direct bond to a polymer chain, wherein $R^4$, $R^6$, $R^7$, $R^9$, $R^{14}$, $R^{15}$, $R^{17}$, $R^{18}$ and $R^{19}$ stand for hydrogen or $C_1-C_4$-alkyl, $R^5$ denotes hydrogen, $C_1-C_4$-alkyl or $NR^6R^7$, $R^8$ denotes $COR^{10}$, $R^{10}$ denotes $NR^{11}R^{12}$, $R^{11}$ denotes $C_1-C_4$-alkyl or aryl, in particular phenyl, $R^{12}$ denotes hydrogen, $C_1-C_4$-alkyl or aryl, in particular phenyl, $R^{13}$ denotes hydrogen, $C_1-C_4$-alkyl or aryl, in particular phenyl, $R^{16}$ denotes hydrogen, $C_1-C_4$-alkyl, $COR^{18}$ or $CONHR^{19}$, m denotes a number from 1 to 3, n denotes a number from 0 to 3, p denotes a number from 2 to 3 and Y denotes O or $NR^{17}$ or $R^{13}$ and $R^{14}$ together denote the atoms required for completing an optionally substituted heterocyclic ring, for example a piperidine, piperazine or morpholine ring, which rings may be substituted, e.g. by $C_1-C_3$-alkyl or by halogen, Z denotes the carbon atoms required for completing a 5-membered or 6-membered aromatic heterocyclic ring optionally with a condensed benzene ring attached, and $Z^\ominus$ denotes an anion, which is absent if an anionic group is already attached to the remainder of the molecule;

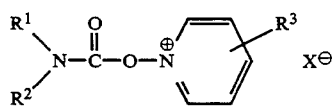 (b)

wherein $R^1$, $R^2$, $R^3$ and $X^\ominus$ have the meaning indicated for formula (a).

There exist diffusible hardeners which have the same hardening action on all the layers within a combination of layers; there also exist non-diffusible, both low molecular weight and high molecular weight hardeners which are limited in their action to the layers in which they are situated. These may be used for particularly strongly cross-linking individual layers, e.g. the protective layer. This is important when the silver halide layer undergoes little hardening due to the increase in silver covering power and it is therefore necessary to improve the mechanical properties by means of the protective layer (EP-A-0 114 699).

Colour photographic recording materials are conventionally processed by development, bleaching, fixing and washing or by development, bleaching, fixing and stabilization without subsequent washing, and bleaching and fixing may be combined in a single process step. Any developer compounds which are capable, in the form of their oxidation product, of reacting with colour couplers to form azomethine or indophenol dyes may be used as colour developer compounds. Suitable colour developer compounds include aromatic compounds of the p-phenylene diamine series having at least one primary amino group, for example: N,N-Dialkyl-p-phenylene diamines such as N,N-diethyl-p-phenylene diamine, 1-(N-ethyl-N-methanesulphonamidoethyl)-3-methyl-p-phenylene diamine, 1-(N-ethyl-N-hydroxyethyl)-3-methyl-p-phenylene diamine and 1-(N-ethyl-N-methoxyethyl)-3-methyl-p-phenylene diamine. Other suitable colour developers are described, for example, in J. Amer. Chem. Soc. 73, 3106 (1951) and G. Haist, Modern Photographic Processing, 1979, John Wiley and Sons, New York, pages 545 et seq.

Colour development may be followed by an acid short stop bath or by washing.

The material is usually bleached and fixed immediately after colour development. The bleaching agents used may be, for example, Fe(III) salts and Fe(III) complex salts such as ferricyanides, dichromates or water-soluble cobalt complexes. Iron-(III) complexes of aminopolycarboxylic acids are especially preferred, in particular e.g. the iron(III) complexes of ethylene diaminotetracetic acid, propylene diaminotetracetic acid, diethylenetriaminopentacetic acid, nitrilotriacetic acid, iminodiacetic acid, N-hydroxyethyl ethylenediaminotriacetic acid and alkyliminodicarboxylic acids and of the corresponding phosphonic acids. Persulphates and peroxides are also suitable bleaching agents, e.g. hydrogen peroxide.

The bleach fixing bath or fixing bath is in most cases followed by washing, which is carried out in counterflow or in several tanks, each with its own water supply.

Advantageous results may be obtained if these steps are followed by a final bath containing little or no formaldehyde.

Washing may also be completely replaced by a stabilizing bath which is normally carried out in counterflow. When formaldehyde is added, this stabilizing bath also functions as a final bath.

EXAMPLE 1

A colour photographic recording material suitable for rapid processing was prepared by applying the following layers in the given sequence to a layer support of paper coated with polyethylene on both sides. The quantities given are based in each case on 1 m². The quantities of silver halide applied are given in the corresponding quantities of $AgNO_3$.

Layer arrangement 1 (Comparison)

Layer 1: (Subbing layer)

0.2 g of gelatine

Layer 2: (blue sensitive layer)
   blue sensitive silver halide emulsion (99.5 mol-% chloride, 0.5 mol-% bromide, mean grain diameter 0.75 μm) of 0.44 g of AgNO₃ with
   1.38 g of gelatine,
   0.95 g of yellow coupler Y-66,
   0.2 g of white coupler W-1 and
   0.29 g of tricresylphosphate (TCP)
Layer 3: (Protective layer)
   1.1 g of gelatine,
   0.06 g of 2,5-dioctyl hydroquinone and
   0.06 g of dibutylphthalate (DBP)
Layer 4: (green sensitive layer)
   green sensitized silver halide emulsion (99.5 mol-% chloride, 0.5 mol-% bromide, mean grain diameter 0.65 μm) of 0.42 g of AgNO₃ with
   1.08 g of gelatine,
   0.41 g of magenta coupler M-3,
   0.16 g of α-(3-t-butyl-4-hydroxyphenoxy)-myristic acid ethyl ester,
   0.08 g of 2,5-dioctylhydroquinone,
   0.34 g of DBP and
   0.04 g of TCP
Layer 5: (UV protective layer)
   1.15 g of gelatine,
   0.6 g of UV absorbent corresponding to the following formula

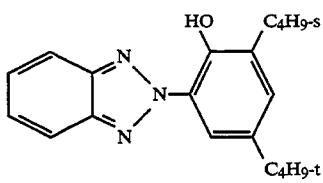

0.045 g of 2,5-dioctylhydroquinone and
   0.04 g of TCP
Layer 6: (red sensitive layer)
   red sensitized silver halide emulsion (99.5 mol-% chloride, 0.5 mol-% bromide, mean grain diameter 0.5 μm) of
   0.39 g of AgNO₃ with
   0.75 g of gelatine,
   0.36 g of cyan coupler C-18 and
   0.36 g of TCP
Layer 7: (UV protective layer)
   0.35 g of gelatine,
   0.15 g of the UV absorbent as in layer 5 and
   0.2 g of TCP
Layer 8: (protective layer)
   0.9 g of gelatine and
   0.3 g of hardener carbamoyl pyridinium salt (CAS Reg. No. 65511-60-1)

The following compound (white coupler W-1) was used in layer 2:

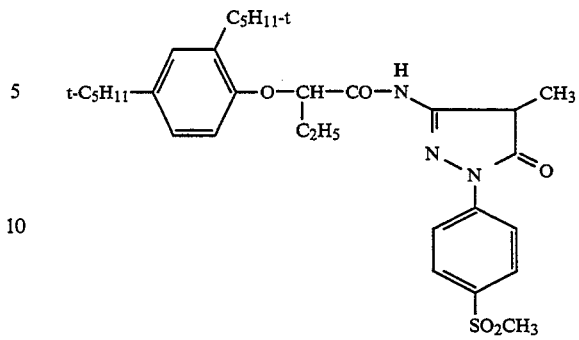

Layer arrangements 2–5

Layer arrangements 2–5 were prepared by the same method as layer arrangement 1 except that Compound I-7 (stabilizer) was added to Layer 5, as may be seen from Table 2. In layer arrangements 2–4 (according to the invention), this stabilizer was added in the form of a common dispersion with dispersing agent II-23 (prepared as described on page 14) and in layer arrangement 5 (comparison) the stabilizer was added in the form of a 1% ethanolic solution.

Layer arrangement 6–10

Layer arrangements 6–10 were prepared by the same method as layer arrangement 1 except that in Layer 4, magenta coupler M-2 was used instead of magenta coupler M-3 in the molar equivalent quantity (0.52 g) and the following silver applications were used per m²:
Layer 2: 0.63 g of AgNO₃ instead of 0.44 g of AgNO₃
Layer 4: 0.45 g of AgNO₃ instead of 0.42 g of AgNO₃
Layer 6: 0.30 g of AgNO₃ instead of 0.39 g of AgNO₃
and the mean grain diameter of the silver halide emulsion in Layer 2 was 0.8 μm (instead of 0.75 μm) and in Layer 4 it was 0.6 μm (instead of 0.65 μm).

In layer arrangements 7–10, Compound I-4 was added as stabilizer to Layer 5, as shown in Table 3. In Layer arrangement 6 (comparison), Layer 5 contained no stabilizer. In layer arrangements 7–9 (according to the invention), the stabilizer was added in the form of a dispersion—compare layer arrangements 2–4. In layer arrangement 10 (comparison), the stabilizer was added in the form of a 1% ethanolic solution.

The samples obtained (layer arrangements 1–10) were exposed to green light for 40 ms behind a graduated wedge and then processed as follows with the processing baths listed below:

| a) Colour developer - 45 s - 35° C. | |
|---|---|
| Triethanolamine | 9.0 g |
| N,N-Diethylhydroxylamine | 4.0 g |
| Diethylene glycol | 0.05 g |
| 3-Methyl-4-amino-N-ethyl-N-methane sulphonamidoethyl-aniline sulphate | 5.0 g |
| Potassium sulphite | 0.2 g |
| Triethylene glycol | 0.05 g |
| Potassium carbonate | 22 g |
| Potassium hydroxide | 0.4 g |
| Ethylene diaminotetracetic acid disodium salt | 2.2 g |
| Potassium chloride | 2.5 g |
| 1,2-Dihydroxybenzene-3,4,6-trisulphonic acid trisodium salt | 0.3 g |
| made up with water to 1000 ml; pH 10.0 | |
| b) Bleach fixing bath - 45 s - 35° C. | |
| Ammonium thiosulphate | 75 g |
| Sodium hydrogen sulphite | 13.5 g |
| Ammonium acetate | 2.0 g |

| -continued | |
|---|---|
| Ethylene diaminotetracetic acid (iron-ammonium salt) | 57 g |
| Ammonia 25% | 9.5 g |
| made up with acetic acid to 1000 ml; pH 5.5 | |
| c) Washing - 2 min - 33° C. | |

Fog (S), sensitivity at density 0.6 above fog (E), gradation ($\gamma_1$; $\gamma_2$) and maximum colour density ($D_{max}$) were then measured. In addition, the percentage increase in colour density was measured in the region of magenta coloured streaks, starting from colour density 1.0 ($\Delta D_{1.0}$). The results are summarized in Tables 2 and 3.

TABLE 2

| Layer arrangement | 1 | 2 | 3 | 4 | 5 |
|---|---|---|---|---|---|
| Compound I-7 | — | 0.2 mg | 0.4 mg | 0.8 mg | (0.8 mg dissolved) |
| Fog S × 1000 | 126 | 127 | 127 | 128 | 127 |
| Sensitivity E | 1352 | 1348 | 1334 | 1327 | 1300 |
| $\gamma_1$ | 181 | 184 | 183 | 181 | 178 |
| $\gamma_2$ | 367 | 367 | 378 | 379 | 360 |
| $D_{max}$ | 2.66 | 2.67 | 2.68 | 2.68 | 2.65 |
| $\Delta D_{1.0}$ (%) | 25 | 21 | 14 | 5 | 6 |

TABLE 3

| Layer arrangement | 6 | 7 | 8 | 9 | 10 |
|---|---|---|---|---|---|
| Compound I-7 | — | 1.0 mg | 1.5 mg | 2.2 mg | (2.20 mg dissolved) |
| Fog S × 1000 | 121 | 121 | 121 | 121 | 119 |
| Sensitivity E | 1641 | 1620 | 1609 | 1603 | 1550 |
| $\gamma_1$ | 176 | 173 | 170 | 172 | 165 |
| $\gamma_2$ | 324 | 322 | 320 | 319 | 310 |
| $D_{max}$ | 2.66 | 2.64 | 2.60 | 2.60 | 2.55 |
| $\Delta D_{1.0}$ (%) | 30 | 20 | 10 | 2 | 1 |

EXAMPLE 2

A colour photographic recording material suitable for rapid processing was prepared by applying the following layers in the given sequence to a layer support of polyethylene terephthalate. The quantities given are based in each case on 1 m². The quantities of silver halide applied are given in the corresponding quantities of $AgNO_3$.

Layer arrangement 11 (Comparison)
Layer 1: (Subbing layer)
  0.4 g of gelatine,
  0.2 g of the UV absorbent used in Example 1, Layer 5 and
  0.25 g of TCP
Layer 2: (blue sensitive layer)
  blue sensitive silver halide emulsion (99.5 mol-% chloride, 0.5 mol-% bromide, mean grain diameter 0.75 μm) of 1.25 g $AgNO_3$ with
  3.92 g of gelatine,
  2.69 g of yellow coupler Y-66
  0.57 g of white coupler W-1 and
  0.82 g of TCP
Layer 3: (protective layer)
  1.1 g of gelatine,
  0.06 g of 2,5-dioctylhydroquinone and
  0.06 g of dibutylphthalate (DBP)
Layer 4: (green sensitive layer)
  green sensitized silver halide emulsion (99.5 mol-% chloride, 0.5 mol-% bromide, mean grain diameter 0.65 μm) of 1.00 g $AgNO_3$ with
  2.57 g of gelatine,
  0.96 g of magenta coupler M-3,
  0.38 g of α-(3-t-butyl-4-hydroxyphenoxy)-myristic acid ethyl ester,
  0.19 g of 2,5-dioctylhydroquinone,
  0.81 g of DBP and
  0.10 g of TCP
Layer 5: (UV protective layer)
  1.15 g of gelatine,
  0.6 g of the UV absorbent corresponding to the formula shown in Example 1, Layer 5,
  0.045 g of 2,5-dioctylhydroquinone and
  0.04 g of TCP
Layer 6: (red sensitive layer)
  red sensitized silver halide emulsion (99.5 mol-% chloride, 0.5 mol-% bromide, mean grain diameter 0.5 μm) of
  0.80 g $AgNO_3$ with
  1.54 g of gelatine,
  0.74 g of cyan coupler C-18 and
  0.74 g of TCP
Layer 7: (UV protective layer)
  0.35 g of gelatine,
  0.15 g of the UV absorbent used in Layer 5 and
  0.2 g of TCP
Layer 8: (protective layer)
  0.9 g of gelatine and
  0.81 g of hardener carbamoyl pyridinium salt (CAS Reg. No. 65511-60-1)

The following compound (white coupler W-1) was used in Layer 2:

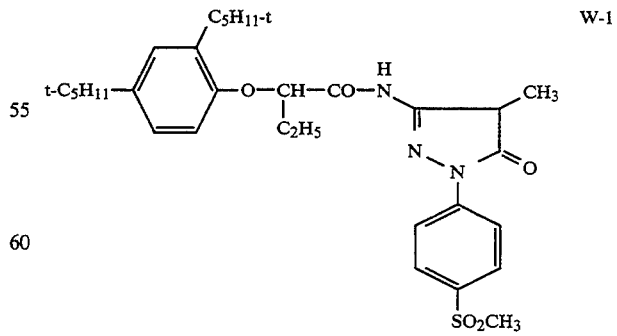

Layer arrangements 12-15
Layer arrangements 12-15 were prepared by the same method as Layer arrangement 11 except that compound I-1 (stabilizer) was added to Layers 3 and 5, as can be seen from Table 4. In Layer arrangements 12-14 (according to the invention), the stabilizer was added in the form of a common dispersion with dispersing agent II-23 (prepared as described on page 14) and in Layer arrangement 5 (Comparison), the stabilizer was added in the form of a 1% ethanolic solution.

Layer arrangements 16-20

Layer arrangements 16-20 were prepared by the same method as Layer arrangement 11 except that in Layer 4, magenta coupler M-2 was used instead of magenta coupler M-3 in the molar equivalent quantity (1.20 g), the following silver applications were used per $m^2$:

Layer 2: 1.10 g of $AgNO_3$ instead of 1.25 g of $AgNO_3$
Layer 4: 0.95 g of $AgNO_3$ instead of 1.00 g of $AgNO_3$
Layer 6: 0.85 g of $AgNO_3$ instead of 0.80 g of $AgNO_3$
and that the mean grain diameter of the silver halide emulsion in Layer 2 was 0.8 μm (instead of 0.75 μm) and in Layer 4 it was 0.6 μm (instead of 0.65 μm).

In Layer of arrangements 17-20, compound I-7 was added as stabilizer to layers 3 and 5, as shown in Table 3. In layer arrangement 16 (comparison), Layer 5 contained no stabilizer. In layer arrangements 17-19 (according to the invention) the stabilizer was added in the form of a dispersion—compare layer arrangements 12-14. In layer arrangement 20 (comparison), the stabilizer was added in the form of a 1% ethanolic solution.

The samples obtained (Layer arrangements 11-20) were exposed to green light behind a graduated wedge for 40 ms and then processed in the processing baths described in Example 1 but the duration of treatment steps a (colour developer) and b (bleach fixing bath) was increased from 45 s to 110 s and the duration of treatment step C (washing) was increased from 2 minutes to 2½ minutes.

Fog (S), sensitivity and density 0.6 above fog (E), gradation ($\gamma_1$; $\gamma_2$) and maximum colour density ($D_{max}$) were then measured. In addition, the percentage increase in colour density was measured in the region of the magenta coloured streaks, starting from colour density 1.0 ($\Delta D_{1.0}$). The results are summarized in Tables 4 and 5.

halide emulsion layer containing a yellow coupler, at least one green sensitive silver halide emulsion layer containing a magenta coupler, at least one red sensitive silver halide emulsion layer containing a cyan coupler and light insensitive layers, wherein in at least one light insensitive layer contains in combination a compound of formula I (stabilizer)

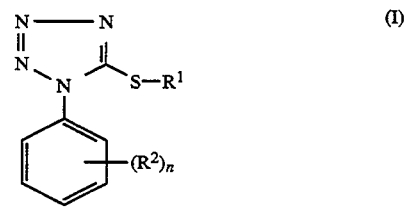

wherein
$R^1$ denotes H or a group which can be split off under alkaline development conditions;
$R^2$ denotes H, halogen, OH, an alkyl having 1 to 4 carbon atoms, an alkoxy having 1 to 4 carbon atoms, $COOR^3$, $CONR^4R^5$, $SO_2NR^4R^5$, NH—$COR^3$, NH—$SO_2$—$R^3$ or NH—CO—$NHR^4$;
$R^3$ denotes an alkyl having 1 to 4 carbon atoms,
$R^4$ and $R^5$ denotes H or a group having the same meaning as $R^3$, and
n denotes 1, 2 or 3, and 1 to 5 times its quantity of a dispersing agent selected from the group consisting of organic compounds containing at least one carboxyl, sulpho, hydroxy and/or quaternary ammonium group and at least one hydrophobic group having at least one alkyl or cycloalkyl group with not less than 10 carbon atoms.

2. Recording material according to claim 1, characterised in that the dispersing agent is an aliphatic, cycloaliphatic or aromatic carboxylic acid having at least one aliphatic or cycloaliphatic group with not less than 10 carbon atoms.

3. Recording material according to claim 2, characterised in that the dispersing agent is a monoester of a succinic acid substituted with a long chain aliphatic

TABLE 4

| Layer arrangement | 11 | 12 | 13 | 14 | 15 |
|---|---|---|---|---|---|
| Compound I-7 | | | | | |
| Layer 3 | — | 0.4 | 0.6 | 0.8 | (0.6 mg dissolved) |
| Layer 5 | — | 0.2 | 0.4 | 0.6 | (0.4 mg dissolved) |
| Fog S × 1000 | 100 | 101 | 100 | 101 | 100 |
| Sensitivity E | 3150 | 3147 | 3152 | 3145 | 3145 |
| $\gamma_1$ | 254 | 253 | 252 | 249 | 235 |
| $\gamma_2$ | 399 | 390 | 391 | 389 | 371 |
| $D_{max}$ | 3.14 | 3.01 | 3.12 | 3.17 | 3.10 |
| $\Delta D_{1.0}$ (%) | 30 | 26 | 10 | 4 | 4 |

TABLE 5

| Layer arrangement | 16 | 17 | 18 | 19 | 20 |
|---|---|---|---|---|---|
| Compound I-7 | | | | | |
| Layer 3 | — | 0.51 | 0.77 | 0.99 | (0.77 mg dissolved) |
| Layer 5 | — | 0.21 | 0.44 | 0.66 | (0.44 mg dissolved) |
| Fog S × 1000 | 102 | 104 | 103 | 102 | 100 |
| Sensitivity E | 3146 | 3140 | 3139 | 3130 | 3110 |
| $\gamma_1$ | 260 | 255 | 251 | 250 | 240 |
| $\gamma_2$ | 402 | 395 | 393 | 390 | 380 |
| $D_{max}$ | 3.18 | 3.16 | 3.11 | 3.10 | 3.08 |
| $\Delta D_{1.0}$ (%) | 35 | 28 | 10 | 8 | 7 |

We claim:

1. Color photographic recording material comprising a layer support and at least one blue sensitive silver group.

4. Recording material according to claim 1, characterised in that the dispersing agent contains a quaternary ammonium group corresponding to the formula

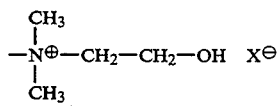

wherein $X^{\ominus}$ stands for an external anion.

5. Recording material according to claim 1, characterised in that the combination of stabilizer and dispersing agent is contained in a light insensitive layer adjacent to the light sensitive silver halide emulsion layer which contains the magenta coupler.

6. The color photographic recording material as claimed in claim 1, wherein $R^1$ is an acyl group derived from a carbonic acid monoester;

$R^2$ is selected from the group consisting of a chlorine atom, a bromine atom, methyl, ethyl, propyl, isopropyl, butyl, methoxymethyl, methylthioethyl, chloroethyl, carboxymethyl-thiomethyl and carboxyethyl; and $R^3$ is selected from the group consisting of methyl, ethyl, propyl, isopropyl, butyl, methoxymethyl, methylthioethyl, chloroethyl, carboxymethyl-thiomethyl and carboxyethyl.

7. The color photographic recording material as claimed in claim 1, wherein $R^1$ is selected from the group consisting of

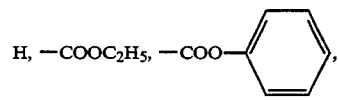

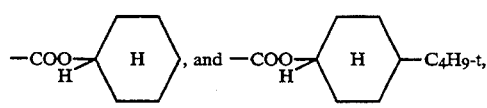

$R^2$ is selected from the group consisting of H; 3—NH—COCH$_3$; 4—CH$_3$; 4—OH; 3—SO$_2$NH$_2$; 3—Cl and 4—CH$_3$; 3,4—di—Cl; 3—OH; 3—NH—CO—NH—CH$_3$; 4—SO$_2$NH$_2$; 4—Cl; 3,4—di—CH$_3$; 4—NH—CO—CH$_2$—O—CH$_3$; 3—NH—COCH$_3$; 4—COOC$_2$H$_5$; 4—NH—CO—(CH$_2$)$_2$—S—CH$_3$; 3—NH—COCH$_2$S—CH$_2$COOH; 3—NH—CO(CH$_2$)$_2$COOH; and 3—NH—CO—CH$_2$—S—CH$_3$.

8. Recording material according to claim 2, wherein the dispersing agent is selected from the group consisting of

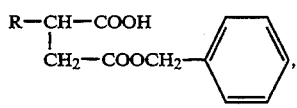

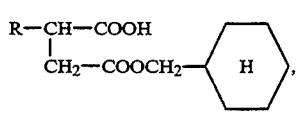

-continued

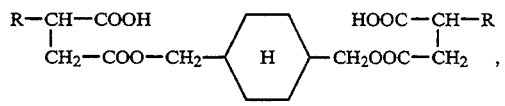

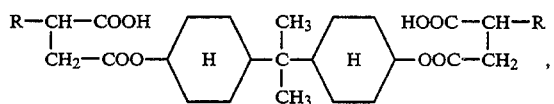

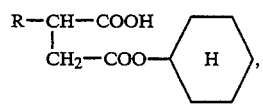

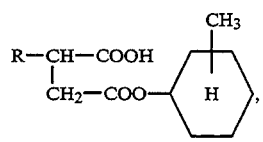

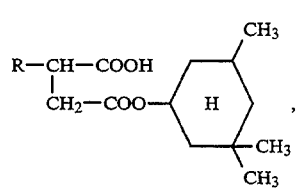

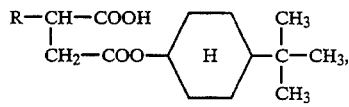

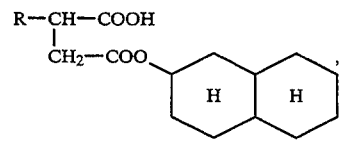

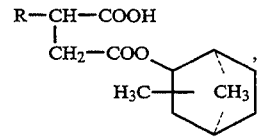

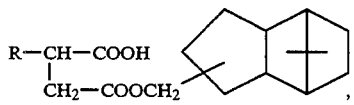

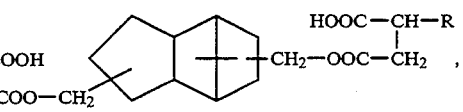

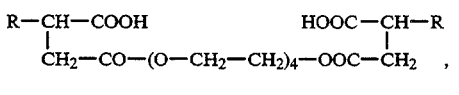

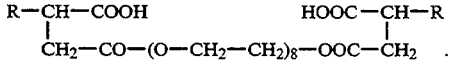

and a mixture thereof; and
wherein R denotes an aliphatic group having at least 6 carbon atoms.

9. The recording material according to claim 8, wherein R is selected from the group consisting of $C_{12}H_{23}$, $C_{15}H_{29}$ and $C_{18}H_{35}$.

10. The recording material according to claim 4, wherein $X^{\ominus}$ is selected from the group consisting of $Cl^{\ominus}$, $NO_3^{\ominus}$ and $\frac{1}{2}(SO_4^{2\ominus})$.

11. The recording material according to claim 1, wherein the quaternary ammonium group is selected from the group consisting of 12. The recording material according to claim 5, wherein the light sensitive layer contains a stabilizer in a quantity of from 0.1 to 5.0 mg/m².

13. The recording material according to claim 5, wherein the light sensitive layer contains a stabilizer in a quantity of from 0.2 to 2.5 mg/m².

14. The recording material according to claim 13, wherein the light insensitive layer is adjacent thereto and further from the support than the green sensitive silver halide emulsion layer.

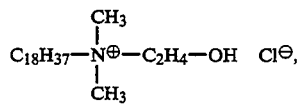

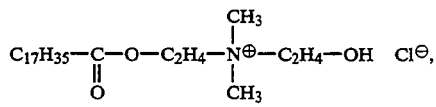

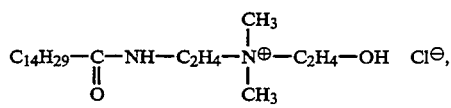

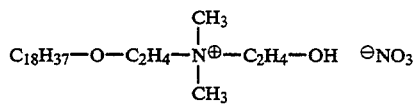

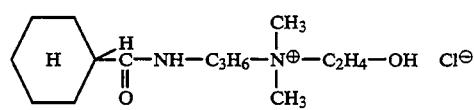

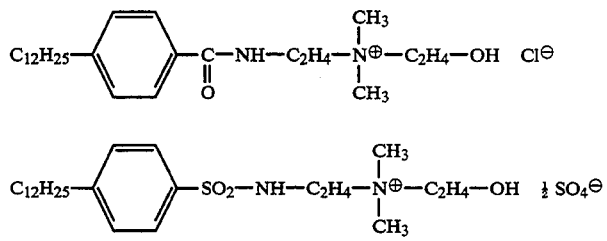

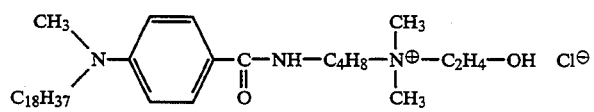

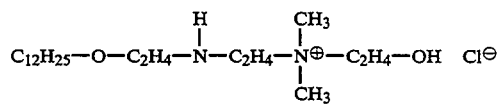

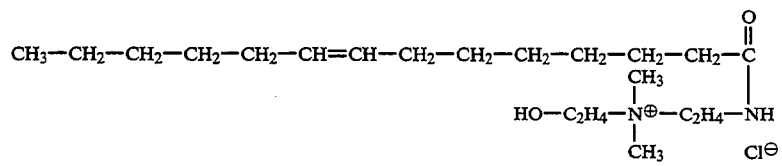

and

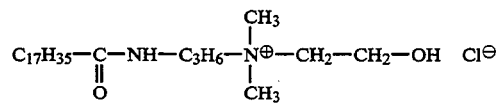

15. The recording material according to claim 5, wherein the said emulsion layer comprises binders and silver halide grains.

16. The recording material according to claim 15, wherein the binder is selected from the group consisting of polyvinyl alcohol, poly-N-vinyl pyrrolidone, polyacrylamides, polyacrylic acid, albumin, casein, cellulose, sugar, starch, alginates and gelatine.

17. The recording material according to claim 5, wherein said blue sensitive, red sensitive and green sensitive silver halide emulsions contain at least 90 mol % of chloride, 0–10 mol % bromide, 0–10 mol % iodide, and 0 to 10 mol % thiocyanate.

18. The recording material according to claim 17, wherein iodide is present from 0.1 to 0.5 mol %, bromide is present from 0.2 to 5 mol % and thiocyanate is present from 0.2 to 5 mol % and wherein the layer has a grain size from 0.3 to 0.9 μm.

* * * * *